United States Patent
Tamiz et al.

(10) Patent No.: US 7,262,211 B2
(45) Date of Patent: Aug. 28, 2007

(54) AROMATIC HETEROCYCLIC NON-COVALENT INHIBITORS OF UROKINASE AND BLOOD VESSEL FORMATION

(75) Inventors: Amir P. Tamiz, San Diego, CA (US); L. Josue Alfaro-Lopez, San Marcos, CA (US); Odile Esther Levy, San Diego, CA (US); Joseph Edward Semple, San Diego, CA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 10/309,781

(22) Filed: Dec. 4, 2002

(65) Prior Publication Data

US 2003/0207842 A1    Nov. 6, 2003

Related U.S. Application Data

(60) Provisional application No. 60/337,100, filed on Dec. 4, 2001.

(51) Int. Cl.
*A61K 31/4412* (2006.01)
*C07D 211/04* (2006.01)

(52) U.S. Cl. .................. 514/346; 546/223; 546/225; 546/245

(58) Field of Classification Search ............... 546/223, 546/225, 245; 514/346
See application file for complete search history.

(56) References Cited

U.S. PATENT DOCUMENTS 6,387,911 B1    5/2002  Burgey et al. ......... 514/255.05
6,455,532 B1    9/2002  Burgey et al. ......... 514/255.02
6,586,405 B2 *  7/2003  Semple et al. ................ 514/19
2002/0004507 A1 1/2002  Cowden et al. ........ 514/255.05

FOREIGN PATENT DOCUMENTS

| WO | 99/26926 | 6/1999 |
| WO | 99/64446 | 12/1999 |
| WO | 00/32574 | * 6/2000 |
| WO | WO2000069826 | * 11/2000 |
| WO | 01/36426 A1 | 5/2001 |
| WO | 01/38323 A1 | 5/2001 |
| WO | 01/87854 A1 | 11/2001 |
| WO | 02/14349 | * 2/2002 |

OTHER PUBLICATIONS

Rosenberg, S., "The Urokinase-type Plasinogen Activator and its Receptor in Cancer". In: Ann. Rep. Med. Chem. 1999, Chapter 12, vol. 34, pp. 121-128.

* cited by examiner

*Primary Examiner*—Rita Desai
(74) *Attorney, Agent, or Firm*—Townsend and Townsend and Crew LLP

(57) ABSTRACT

Novel compounds having activity as non-covalent inhibitors of urokinase and having activity in reducing or inhibiting blood vessel formation are provided. These compounds have at a group having a guanidino moiety or derivative thereof. These compounds are useful in vitro for monitoring plasminogen activator levels and in vivo in treatment of conditions which are ameliorated by inhibition of or decreased activity of urokinase and in treating pathologic conditions wherein blood vessel formation is related to a pathologic condition.

19 Claims, 9 Drawing Sheets

Figure 8

| Compound | Structure |
|---|---|
| A | (benzyl-SO₂-NH-[3-position of 2-oxo-pyridin-1-yl]-CH₂-C(O)-NH-CH₂-[4-guanidinophenyl]) |
| B | (4-iodobenzyl-SO₂-NH-[3-position of 2-oxo-pyridin-1-yl]-CH₂-C(O)-NH-CH₂-[4-guanidinophenyl]) |
| C | (4-iodobenzyl-SO₂-NH-[3-position of 2-oxo-pyridin-1-yl]-CH(CH₃)-C(O)-NH-CH₂-[4-guanidinophenyl]) |
| D | (benzyl-SO₂-NH-[3-position of 2-oxo-pyridin-1-yl]-CH(CH₃)-C(O)-NH-CH₂-[4-guanidinophenyl]) |
| E | (4-iodophenyl-SO₂-NH-[3-position of 2-oxo-pyridin-1-yl]-CH(CH₃)-C(O)-NH-CH₂-[4-guanidinophenyl]) |
| F | (4-bromobenzyl-SO₂-NH-[3-position of 2-oxo-pyridin-1-yl]-CH(CH₃)-C(O)-NH-CH₂-[4-guanidinophenyl]) |

Figure 9
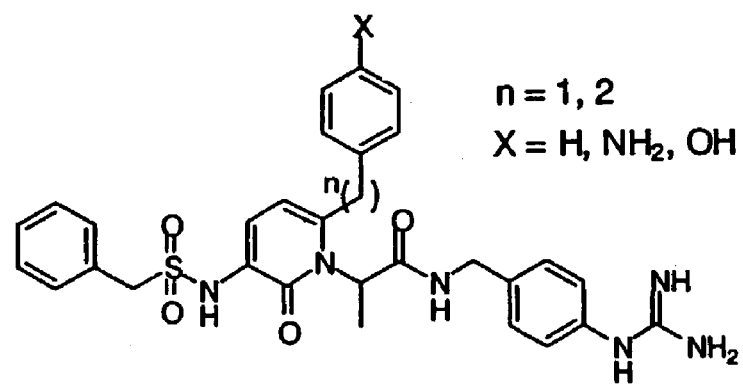
n = 1, 2
X = H, NH₂, OH
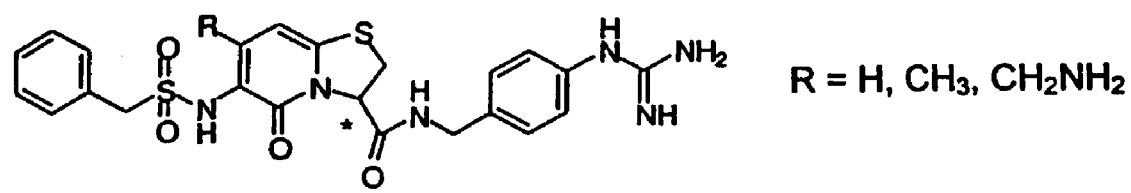
R = H, CH₃, CH₂NH₂
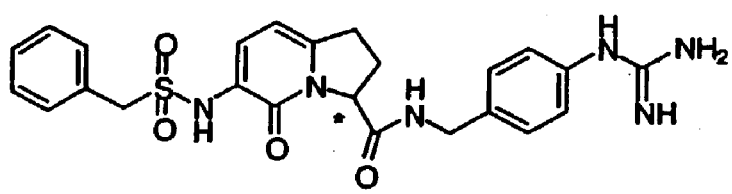
* Both R and S isomers

AROMATIC HETEROCYCLIC NON-COVALENT INHIBITORS OF UROKINASE AND BLOOD VESSEL FORMATION

CROSS REFERENCE TO RELATED APPLICATIONS

This patent application is a continuation-in-part and claims priority from U.S. Provisional Application Ser. No. 60/337,100 filed Dec. 4, 2001, the entirety of the disclosure of which is incorporated into the present application by reference.

FIELD OF THE INVENTION

Urokinase is an enzyme involved in the metastasis of tumor cells, neovascularization, and other activities. One aspect of the present invention is to provide novel compounds that can be used to inhibit the activity of urokinase and thereby attenuate its deleterious effects. Another aspect of the present invention is to provide novel compounds which inhibit blood vessel formation, particularly blood vessel formation related to a pathologic condition.

BACKGROUND AND INTRODUCTION TO THE INVENTION

Urinary-type plasminogen activator (uPA; urokinase) is a serine protease within the trypsin/chymotrypsin family. In its physiological state, uPA is found in three forms: single chain pro-uPA, two chain uPA, and low molecular weight uPA (lacks N-terminal domains). The zymogen, pro-uPA, is converted to u-PA by cleavage of the peptide bond at K158-I159. The resultant two chain uPA is linked by disulfide bridges, has an $M_r$ of about 50 kD, and a C-terminal serine proteinase domain.

The activity of uPA is focused to cell surfaces upon binding to its receptor, uPAR. uPAR is a single-chain glycosyl phosphatidyl inositol (GPI)-anchored membrane receptor. The N-terminal 92 amino acids of uPAR play a dominant role in binding to uPA and pro-uPA. Receptor for uPA has been located on T-cells, NK cells, monocytes, and neutrophils, as well as vascular endothelial cells, fibroblasts, smooth muscle cells, keratinocytes, placental trophoblasts, hepatocytes, and a wide variety of tumor cells.

After conversion of pro-uPA to uPA, which occurs primarily at the uPAR on the cell surface, uPA activates plasminogen to plasmin. Activation occurs upon cleavage at residues PGR-VV for human plasminogen, or at residues SGR-IV for bovine plasminogen. Because plasminogen also is present on the cell surface, this activation cascade focuses the activity of uPA and plasmin on the plasma membrane. Plasmin has many roles, including activation of additional uPA and other enzymes, digestion of fibrin, and digestion of components of the extracellular matrix (ECM). Digestion of the ECM surrounding a tumor removes the ECM as a physical barrier to metastasizing cells, which are then free to leave primary tumors and invade secondary sites. A review of the role of the uPA/uPAR system in cancer metastasis is provided in "The Urokinase-type Plasminogen Activator System in Cancer Metastasis: A Review", Andreasen et al., Int. J. Canc. 72:1-22 (1997).

A correlation between a high level of uPA and a high rate of metastasis, and poor prognosis, has been noted in certain tumors, especially breast cancer [Quax et al., J. Cell Biol. 115:191-199 (1991); Duffy et al., Cancer Res. 50:6827-6829 (1990)]. For instance, tumors of the lung [Oka et al., Cancer Res. 51:3522-3525 (1991)], bladder [Hasui et al., Int. J. Cancer 50:871-873 (1992)], stomach [Nekarda et al., Lancet 343:117 (1994)], cervical cancer [Kobayashi et al., Cancer Res. 54:6539-6548 (1994)], ovary [Kuhn et al., Gynecol. Oncol. 55:401-409 (1994)], kidney [Hofmann et al., Cancer 78:487-492 (1996)], brain [Bindahl et al., J. Neuro-Oncol. 22:101-110 (1994)], and soft tissue sarcoma [Choong et al., Int. J. Cancer (Pred. Oncol.) 69:268-272 (1996)] have exhibited a high level of uPA and/or uPA activity and a high rate of metastases. Overproduction of uPA has been reported to result in increased skeletal metastasis by prostate cancer cells in vivo [Achbarou et al., Cancer Res. 54:2372-2377 (1994)].

Inhibition or lowering of uPA activity, or disruption/inhibition of the interaction between uPA and its receptor (uPAR) has been shown to have a positive effect on maintenance of the extracellular matrix and an inhibitory effect on metastasis [Ossowski and Reich, Cell 35:611-619 (1983); Ossowski, Cell 52:321-328 (1988); Ossowski, J. Cell Biol. 107:2437-2445 (1988); Wilhelm et al., Clin. Exp. Metastasis 13:296-302 (1995); Achbarou et al., Cancer Res. 54:2372-2377 (1994); Crowley et al., Proc. Natl. Acad. Sci. USA 90:5021-5025 (1993); Kook et al., EMBO J. 13:3983-3991 (1994)]. The results of such experimental studies suggest that uPA-catalyzed plasminogen activation is rate-limiting for tumor progression, local tumor invasion and/or formation of distant metastasis. [Andreasen et al., Int. J. Canc. 72:1-22 (1997)].

The effects of the uPA system on cell migration and invasion are thought to be due to both a proteolytic effect of plasmin-mediated degradation of the extracellular matrix, as well as more a direct interaction of the uPA receptor with components of the extracellular matrix. Degradation of the extracellular matrix permits a metastasizing cell to invade the matrix, whereas interaction between uPA receptor and the matrix itself assists a cell in its migration. Localization of the uPA/plasmin system on the cell surface, or the leading edge of metastasizing cells, is consistent with the postulated role of uPA in metastasis [Plesner et al., Stem Cells 15:398-408 (1997)].

Interaction of uPAR with vitronectin, a component of the extracellular matrix, mediates cell adhesion and can be enhanced when uPAR is bound by uPA. Cell surface adhesion molecules, integrins, also appear to be involved in this adhesion function, particularly beta-1 and beta-2 integrins [Paysant et al., Br. J. Haematol. 100:45-51 (1998); Simon et al., Blood 88:3185-3194 (1996)]. The CD11b/CD18 integrin can associate with the uPA-uPAR complex and promote adhesion of cells bearing these receptors, e.g., neutrophils, leukocytes.

The uPA/uPAR system also is involved in the establishment of new vasculature, or neovascularization.

Establishment of new vasculature is required for sustaining primary and metastatic tumor growth. Pathological neovascularization also is a characteristic of retinal disease, rubeosis iritis, proliferative vitreo retinopathy inflammatory disease, diabetic retinopathy, chronic uveitis, Fuch's heterochromic iridocyclitis, neovascular glaucoma, corneal or optic nerve neovascularization, vascular disease, pterygium, glaucoma surgery bleb failure, hyperkeratosis, cheloid and polyp formation (see EP 451,130). Undesired angiogenesis also can occur in the following conditions or can be a result of the following activities: macular degeneration, retinopathy of prematurity, corneal graft rejection, retrolental fibroplasia, epidemic keratoconjunctivitis, Vitamin A deficiency, contact lens overwear, atopic keratitis, superior limbic keratitis, pterygium keratitis sicca, sogrens disease, acne rosacea, phylectenulosis, syphilis, Mycobacteria infections other than leprosy, lipid degeneration, chemical burns, bacterial or fungal ulcers, Herpes simplex or zoster infections, protozoan infections, Kaposi's sarcoma, Mooren ulcer, Terrien's marginal degeneration, marginal keratolysis, trauma, rheumatoid arthritis, systemic lupus, polyarteritis, Wegeners sarcoidosis, sleritis, Steven's Johnson disease, radial keratotomy, sickle cell anemia, sarcoid, pseudoxanthoma elasticum, Pagets disease, vein or artery occlusion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Wever-Rendu, solid tumors, blood borne tumors, AIDS, ocular neovascular disease, osteoarthritis, chronic inflammation, Crohn's disease, ulcerative colitis, tumors of rhabdomyosarcoma, tumors of retinoblastoma, tumors of Ewing sarcoma, tumors of neuroblastoma, tumors of osteosarcoma, leukemia, psoriasis, atherosclerosis, pemphigoid, as recited in U.S. Pat. No. 5,712,291.

An antagonist of uPA/uPAR binding (EGF-like domain of uPA fused to Fc of IgG) was said to inhibit neovascularization and growth of the murine B16 melanoma. [Min et al., Cancer Res. 56:2428-2433 (1996)]. Consistent with this finding is the correlation noted between microvessel density, vascular invasion and uPA levels in breast carcinomas [Hildenbrand et al., Brit. J. Cancer 72:818-823 (1995)]. The known uPA inhibitor amiloride also was said to inhibit a variety of neovascularization pathologies [Glaser et al., EP 451,130; Avery et al., Arch. Ophthalmol. 108:1474-1476 (1990)].

There are two primary physiological inhibitors of uPA, PAI-1 and PAI-2, which are members of the serpin family of proteinase inhibitors. The binding of serpins to their cognate proteases involves a large number of interactions between amino acids of each protein, including those in the serpin reactive loop (Ser-Ala-Arg-Met-Ala (SEQ. ID. NO. 1) for PAI-1, Thr-Gly-Arg-Thr-Gly (SEQ. ID. NO. 2) for PAI-2). Introduction of exogenous PAI-2 into experimental animals was reported to inhibit the rate of lung metastasis [Evans and Lin, Amer. Surg. 61:692-697 (1995); Mueller et al., Proc. Natl. Acad. Sci. USA 92:205-209 (1995)]. The ability of PAI-1 to inhibit metastasis has not yet been consistently shown. The gene for PAI-1, and means for its recombinant expression, are disclosed in Loskutoff et al., U.S. Pat. No. 4,952,512. Recombinant and native human PAI-2 is disclosed in Stephens et al., U.S. Pat. No. 5,422,090.

The most widely studied uPA inhibitors may be within the 4-substituted benzo[b]thiophene-2-carboxamidine class of inhibitors, of which B428 (4-iodo-benzo[b]thiophene-2-carboxamidine) and B623 are members [Towle et al., Cancer Res. 53:2553-2559 (1993); Bridges et al., Bioorg. Med. Chem. 1:403-410 (1993); Bridges et al., U.S. Pat. No. 5,340,833]. Infusion of B428 in experimental rats inoculated with tumor cells was said to inhibit uPAR gene expression, decrease the primary tumor volume and decrease metastases [Xing et al., Cancer Res. 57:3585-3593 (1997)]. Daily intraperitoneal treatment of mice bearing tumors with B428 or B623 was said to block metastasis to muscle and fat, but did not inhibit tumor-induced angiogenesis or reduce the rate of spontaneous lung metastasis. In fact, B623 enhanced the formation of lung metastasis (Alonso et al., Breast Cancer Res. Treat. 40:209-223 (1996)]. Infusion of B428 in a syngeneic model of rat prostate cancer also lead to a decrease in primary tumor volume and tumor weight, and a decrease in metastasis [Rabbani et al., Int. J. Cancer 63:840-845 (1995)].

Other known inhibitors of uPA include p-aminobenzamidine, which is a competitive inhibitor of uPA, and amiloride. Both compounds have been shown to reduce tumor size in experimental animals [Jankan et al., Cancer Res. 57:559-563 (1997); Billstrom et al., Int. J. Cancer 61:542-547 (1995)]. Recently, epigallo-cathecin-3 gallate (EGCG), a polyphenol found in green tea, was reported to bind uPA and inhibit its activity [Jankun et al., Nature 387:561 (1997)]. Those researchers concluded EGCG is a weaker inhibitor of uPA than amiloride, but suggested EGCG can be consumed in much higher doses than amiloride without toxic effect. A competitive inhibitor of uPA, α-N-benzylsulfonyl-p-aminophenylalanine, is disclosed by Pye et al. in U.S. Pat. No. 4,165,258.

Other approaches at inhibiting the uPA/uPAR system include development of a bifunctional hybrid molecule consisting of the uPAR-binding domain of uPA and PAI-2, which is said to inhibit uPA and bind uPAR in vitro [Ballance et al., Eur. J. Biochem. 207:177-183 (1992)]. Antagonists of uPAR also have been studied [Doyle and Rosenberg, U.S. Pat. No. 5,656,726; Min et al., Cancer Res. 56:2428-2433 (1996)], as have antisense oligonucleotides complementary to uPA [Wilhelm et al., Clin. Exp. Metast. 13:296-302 (1995); Iversen and Scholar, U.S. Pat. No. 5,552,390]. Antibodies directed against uPAR, and said to inhibit the binding of uPA to uPAR, are disclosed by Dano et al. in U.S. Pat. No. 5,519,120. Small molecules said to inhibit urokinase, along with a variety of other serine proteases, include those disclosed by Abe et al. in U.S. Pat. No. 5,508,385 and U.S. Pat. No. 5,153,176, and by Takano et al. in J. Pharmacol. Exp. Therapeut. 271:1027-1033 (1994).

Compounds have been developed to directly inhibit the binding of uPA to UPAR (Crowley et al., Proc. Natl. Acad. Sci. USA 90:5021-5025 (1993); Goodson et al., Proc. Natl. Acad. Sci. USA 91:7129-7133 (1994); Kobayashi et al., Brit. J. Cancer 67:537-544 (1993), and Int. J. Cancer 57:727-73f3 (1994), and J. Biol. Chem. 270:8361-8366 (1995); Lu et al., FEBS Lett. 356:56-59 (1994) and FEBS Lett. 380: 21-24 (1996)].

Additionally, pro-hepatocyte growth factor (HGF), a cell migration stimulating protein, is a substrate of uPA [Naldinie et al., EMBO J. 11:4825-4833 (1992)]. Direct cleavage of a 66 kDa extracellular matrix protein and fibronectin by uPA also has been reported, which suggests a more direct role for uPA in facilitating cell migration [Quigley et al., Proc. Natl. Acad. Sci. 84:2776-2780 (1987)]. Thus, inhibition of uPA may affect these activities, as well.

SUMMARY OF THE INVENTION

The present invention is directed to novel peptidic non-covalent urokinase inhibitors. The compounds have at P1 a group having a guanidino moiety or derivative thereof. These compounds have activity as potent inhibitors of urokinase and thereby are useful in decreasing its deleterious effects. Compounds of the present invention are active in inhibiting blood vessel formation, particularly that related to a pathologic process.

Thus in one aspect, the present invention is directed to compounds of the formula (I):

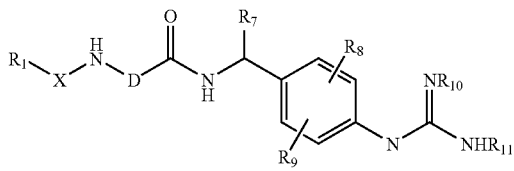

(a) X is selected from the group consisting of —S(O)$_2$—, —N(R')—S(O)$_2$—, —C(=O)—, —OC(=O)—, —NH—C(=O)—, —P(O)(R')—, and a direct link, wherein R' is independently hydrogen, alkyl of 1 to about 4 carbon atoms, aryl of about 6 to about 14 carbon atoms or aralkyl of about 7 to about 16 carbon atoms, with the proviso that when X is —P(O)(R')—, then R' is not hydrogen;

(b) R$_1$ is selected from the group consisting of:

(1) alkyl of 1 to about 12 carbon atoms which is unsubstituted or substituted with 1 or 2 substituents selected from the group consisting of Y$_1$ and Y$_2$, (2) alkyl of 1 to about 3 carbon atoms substituted with cycloalkyl of about 3 to about 8 carbon atoms which is unsubstituted or substituted with 1 to 3 substituents selected from the group consisting of Y$_1$, Y$_2$, and Y$_3$, (3) cycloalkyl of 3 to about 15 carbon atoms, which is unsubstituted or mono-, di-, or tri-substituted on the ring with 1 to 3 substituents selected from the group consisting of Y$_1$, Y$_2$, and Y$_3$, (4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is unsubstituted or mono-, di-, or tri-substituted on the ring with 1 to 3 substituents selected from the group consisting of Y$_1$, Y$_2$, and Y$_3$, (5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, including,

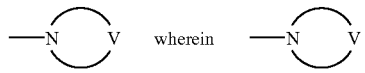

is a 5 to 7 member heterocycle having 3 to 6 ring carbon atoms, where V is —CH$_2$—, —O—, —S(=O)—, —S(O)$_2$— or —S—, which is unsubstituted or mono-, di-, or tri-substituted on the ring carbons with 1 to 3 substituents selected from the group consisting of Y$_1$, Y$_2$, and Y$_3$, (6) alkenyl of 2 to about 6 carbon atoms which is unsubstituted or substituted with cycloalkyl of about 3 to about 8 carbon atoms, which is unsubstituted or mono-, di-, or tri-substituted on the ring with 1 to 3 substituents selected from the group consisting of Y$_1$, Y$_2$, and Y$_3$, (7) aryl of about 6 to about 14 carbon atoms which is unsubstituted or mono-, di- or tri-substituted with 1 to 3 substituents selected from the group consisting of Y$_1$, Y$_2$, and Y$_3$, (8) heteroaryl of about 5 to about 14 ring atoms with the ring atoms selected from carbon and heteroatoms, wherein the heteroatoms are selected from oxygen, nitrogen, and sulfur, and which is unsubstituted or mono-, di- or tri-substituted with 1 to 3 substituents selected from the group consisting of Y$_1$, Y$_2$, and Y$_3$, (9) aralkyl of about 7 to about 15 carbon atoms which is unsubstituted or substituted on the alkyl chain with hydroxy or halogen and which is unsubstituted or mono-, di-, or tri-substituted on the aryl ring with 1 to 3 substituents selected from the group consisting of Y$_1$, Y$_2$, and Y$_3$,

(10) heteroaralkyl of about 5 to about 14 ring atoms with the ring atoms selected from carbon and heteroatoms, wherein the heteroatoms are selected from oxygen, nitrogen, and sulfur, which is unsubstituted or substituted on the alkyl chain with hydroxy or halogen and which is unsubstituted on the ring or mono-, di- or tri-substituted on the ring with 1 to 3 substituents selected from the group consisting of Y$_1$, Y$_2$, and Y$_3$,

(11) aralkenyl of about 8 to about 16 carbon atoms which is unsubstituted or mono-, di-, or tri-substituted on the aryl ring with 1 to 3 substituents selected from the group consisting of Y$_1$, Y$_2$, and Y$_3$,

(12) heteroaralkenyl of about 5 to about 14 ring atoms with the ring atoms selected from carbon and heteroatoms, wherein the heteroatoms are selected from oxygen, nitrogen, and sulfur, and which is unsubstituted or mono-, di- or tri-substituted on the ring carbons with 1 to 3 substituents selected from the group consisting of Y$_1$, Y$_2$, and Y$_3$,

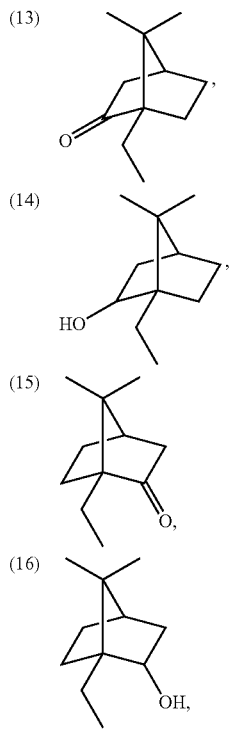

(17) fused carbocyclic alkyl of about 9 to about 15 carbon atoms,

(18) difluoromethyl or perfluoroalkyl of 1 to about 12 carbon atoms,

(19) perfluoroaryl of about 6 to about 14 carbon atoms,

(20) perfluoroaralkyl of about 7 to about 15 carbon atoms, and

(21) hydrogen when X is a direct link;
wherein each $Y_1$, $Y_2$, and $Y_3$ is independently selected and is
(i) selected from the group consisting of halogen, cyano, nitro, tetrazolyl, guanidino, amidino, methylguanidino, —$CF_3$, —$CF_2CF_3$, —$CH(CF_3)_2$, —$C(OH)(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —$OH$, —$NH_2$, —$NHZ_1$, —$NZ_1Z_2$, —$C(=NH)NH_2$, —$C(=NOH)NH_2$, —N-morpholino, and —$S(O)_m(CF_2)_qCF_3$, wherein m is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 ring atoms, aralkyl of about 7 to about 15 carbon atoms, and heteroaralkyl of about 5 to about 14 ring atoms, or
(ii) $Y_1$ and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl of 1 to about 12 carbon atoms, aryl of about 6 to about 14 carbon atoms, heteroaryl of about 5 to about 14 ring atoms, aralkyl of about 7 to about 15 carbon atoms, and heteroaralkyl of about 5 to about 14 ring atoms;
(c) D is

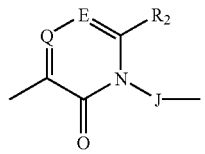

wherein
(1) E is —N— or —$C(R_3)$—;
(2) Q is —N— or —$C(R_4)$—;
(3) $R_2$, $R_3$ and $R_4$ are independently selected and are selected from the group consisting of hydrogen, hydroxy, alkyl of 1 to about 8 carbon atoms, cycloalkyl of 3 to about 8 carbon atoms, alkoxy of 1 to about 8 carbon atoms, alkyl of 1 to about 8 carbon atoms substituted with hydroxy or —$NH_2$ trifluoromethyl, alkyl of 1 to about 8 carbon atoms substituted with cycloalkyl of 3 to about 8 carbon atoms, aralkyl of 7 to about 15 carbon atoms which is unsubstituted or substituted with 1 to 3 substituents independently selected from the group consisting of $Y_1$, $Y_2$ and $Y_3$; phenyl substituted with $Y_1$, a saturated 5 or 6-membered heterocyclic ring having 1 to 2 ring nitrogen atoms and the remainder of the ring atoms carbon atoms, —$NHR_5$, —$S(O)_tR_5$, and —$C(O)OR_5$; or $R_2$ is halogen;
(4) t is 0, 1 or 2;
(5) $R_5$ is selected from the group consisting of hydrogen, alkyl of 1 to about 6 carbon atoms, aryl of 6 to about 14 carbon atoms, which is unsubstituted or mono-, di-, or tri-substituted with 1 to 3 substituents selected from the group consisting of $Y_1$, $Y_2$ and $Y_3$; and aralkyl of about 7 to about 15 carbon atoms which is unsubstituted or substituted on the alkyl chain with hydroxy or halogen and which is unsubstituted or mono-, di- or tri-substituted on the aryl ring with 1 to 3 substituents selected from the group consisting of $Y_1$, $Y_2$ and $Y_3$;
(6) alternatively E is —$C(R_3)$— and $R_2$ and $R_3$ are taken together to form a 5- or 6-membered aromatic ring which is unsubstituted or is substituted with $Y_1$;
(7) J is —$C(R_{6a})(R_{6b})$— wherein (i) $R_{6a}$ is in the S configuration and is selected from the group consisting of —$CH_3$, —$CH_2CH_3$, —$CH_2$—S—$CH_3$, —$CH_2OH$, —$CH_2CN$, —$CH_2C\equiv CH$, —$CH_2CH=CH_2$, and —$CH=CH_2$ and $R_{6b}$ is hydrogen; (ii) $R_{6a}$ and $R_{6b}$ are independently hydrogen or lower alkyl of 1 to about 3 carbon atoms; or (iii) $R_{6a}$ and $R_{6b}$ are selected together and are —$(CH2)_k$— wherein k is 5 or 6 to give a spirocycloalkyl group; or (iv) J and $R_2$ are taken together as set forth in (8); and
(8) alternatively J and $R_2$ selected together are

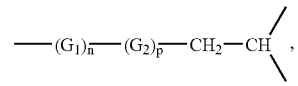

wherein $G_1$ and $G_2$ are independently —$(CH_2)$— or a heteroatom selected from the group consisting of sulfur, oxygen and nitrogen, provided that $G_1$ and $G_2$ are not both heteroatoms, n is 0 or 1 and p is 0 or 1; to give D as

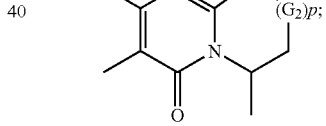

(d) $R_7$ is hydrogen or alkyl of 1 to about 4 carbon atoms;
(e) $R_8$ and $R_9$ are independently selected from the group consisting of hydrogen, hydroxy, halogen, alkyl of 1 to about 6 carbon atoms, alkyl of 1 to about 4 carbon atoms substituted with alkoxy of 1 to about 4 carbon atoms, alkoxy of 1 to about 6 carbon atoms, and trifluoromethyl;
(f) $R_{10}$ and $R_{11}$ are independently selected from the group consisting of hydrogen, hydroxy, alkoxy of 1 to about 3 carbon atoms, trihydrocarbylsilyl of 3 to about 16 carbon atoms, alkyl of 1 to about 3 carbon atoms and —$C(=O)R_{12}$ with the proviso that $R_{10}$ and $R_{11}$ are not both hydroxy or alkoxy; and $R_{12}$ is hydrogen, alkyl of 1 to about 6 carbon atoms, alkoxy of 1 to about 6 carbon atoms or —$(CF_2)_jCF_3$ wherein j is 0, 1, 2 or 3; with the proviso that, when Q is —N—, then X is not —$S(O)_2$—; and pharmaceutically acceptable salts thereof.

The compounds of the present invention can be divided into parts termed $P_1$, $P_2$, $P_3$ and $P_4$ as shown in the following formula Ia:

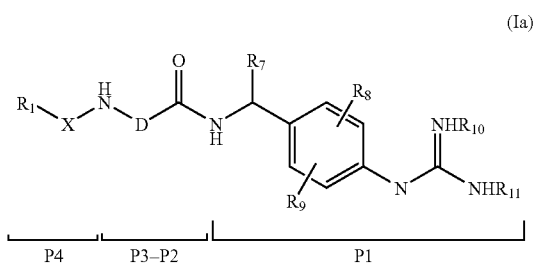

(Ia)

wherein X, $R_1$, D, $R_7$, $R_8$, $R_9$, $R_{10}$ and $R_{11}$ are as defined in connection with formula (I).

Among other factors, the present invention is based on our finding that the novel compounds of our invention are active as inhibitors of urokinase. Compounds of the present invention exhibit activity in inhibiting angiogenesis.

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for inhibition of urokinase.

Definitions

In accordance with the present invention and as used herein, the following terms are defined to have following meanings, unless explicitly stated otherwise:

The term "alkenyl" refers to unsaturated aliphatic groups having at least one double bond.

The term "alkyl" refers to saturated aliphatic groups including straight-chain, branched-chain and cyclic (including polycyclic) groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aralkenyl" refers to an alkenyl group substituted with an aryl group. Preferably the alkenyl group has from 2 to about 6 carbon atoms.

The term "aralkyl" refers to an alkyl group substituted with an aryl group. Suitable aralkyl groups include benzyl, phenethyl, and the like, all of which may be optionally substituted. Preferably the alkyl group has from 1 to about 6 carbon atoms.

The term "aryl" refers to an aromatic group which has at least one ring having a conjugated pi electron system and includes a carbocyclic aryl, heterocyclic aryl and biaryl groups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to both natural, unnatural amino acids in their D and L stereo isomers if their structures allow such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, demosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is H or a carbon containing substituent; or (2)

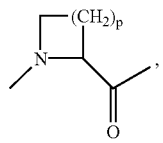

wherein p is 1, 2 or 3 representing the azetidinecarboxylic acid, proline or pipecolic acid residues, respectively.

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, difluoromethyl, nitro, and cyano. Substituted naphthyl refers to naphthyl, more preferably 1- or 2-naphthyl, substituted by $Y_1$, $Y_2$ and/or $Y_3$ as defined in connection with formula (I) hereinabove.

"Cycloalkenyl" refers to a cyclic alkenyl group. Suitable cycloalkenyl groups include, for example, cyclopentenyl and cyclohexenyl.

"Cycloalkyl" refers to a cyclic alkyl group having at least one ring and includes polycyclic groups, including fused ring cyclic alkyl groups. Suitable cycloalkyl groups include, for example, cyclohexyl, cyclopropyl, cyclopentyl, and cycloheptyl.

"Cyclohexylmethyl" refers to a cyclohexyl group attached to $CH_2$.

"Fused carbocyclic" refers to a multicyclic fused carbocyclic ring having both aromatic and non-aromatic rings. Suitable fused carbocyclic rings include fluorenyl, tetralin and the like.

"Fused carbocyclic alkyl" refers to an alkyl group substituted with a fused carbocyclic ring moiety, preferably a multicyclic fused carbocyclic ring including both aromatic and non-aromatic rings. Suitable fused carbocyclic alkyl groups include fluorenylmethyl, and the like.

The term "halogen" refers to fluorine, chlorine, bromine and iodine.

"Heteroaralkenyl" refers to an alkenyl group substituted with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkenyl group has from 2 to about 6 carbon atoms.

"Heteroaralkyl" refers to an alkyl group substituted with a heteroaryl, such as picolyl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from 1 to about 6 carbon atoms.

"Heteroaryl" refers to aromatic groups having from 1 to 14 carbon atoms and the remainder of the ring atoms are heteroatoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, and $S(O)_i$, wherein i is 0, 1 or 2, and suitable heterocyclic aryls include furanyl, thienyl, pyridyl, pyrrolyl, pyrimidyl, pyrazinyl, imidazolyl, and the like.

"Heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heterocycloalkyl" refers to an alkyl group substituted with a heterocyclo group, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from about 1 to about 6 carbon atoms.

The term "lower" referred to herein in connection with organic radicals or groups defines such radicals or groups with one and up to and including 5 carbon atoms, preferably up to and including 4 carbon atoms, and advantageously one or two carbon atoms. Such radicals or groups may be straight chain or branched chain.

"Perfluoroalkyl" refers to an alkyl group which has every hydrogen replaced with fluorine.

"Perfluoroaryl" refers to an aryl group which has every hydrogen replaced with fluorine.

"Perfluoroarylalkyl" refers to an aralkyl group in which every hydrogen on the aryl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

"AcN", $CH_3CN$ or "MeCN" refers to acetonitrile.
"$Ac_2O$" refers to acetic anhydride.
"AcOH" refers to acetic acid.
"AIBN" refers to 2,2'-azobisisobutyronitrile.
"Bn" refers to benzyl.
"$BnSO_2Cl$" refers to benzylsulfonylchloride.
"Boc" refers to t-butoxycarbonyl.
"$Boc_2O$" refers to Boc anhydride (di-tert-butyl carbonate).
"BOC-ON" refers to 2-(tert-butoxycarbonyloxyamino)-2-phenylacetonitrile.
"$BzlSO_2$" refers to benzylsulfonyl.
"Cbz" or "CBz" refers to benzyloxycarbonyl.
"$CNNH_2$" or "$H_2NCN$" refers to cyanamide.
"$CsCo_3$" refers to cesium carbonate.
"DCA" refers to dichloroacetic acid.
"DCC" refers to N,N'-dicyclohexylcarbodiimide.
"DCE" is 1,2-dichloroethane.
"DCM" or "$CH_2Cl_2$" refers to dichloromethane (methylene chloride).
"DIEA" refers to diisopropylethylamine.
"DMF" refers to N,N-dimethylformamide.
"DMSO" refers to dimethyl sulfoxide.
"DMAP" refers to 4-N,N-dimethylaminopyridine.
"EDC" refers to 1-ethyl-3-(3-dimethylamino-propyl) carbodiimide hydrochloride salt.
"$Et_3N$" or "TEA" refers to triethylamine.
"EtOAc" refers to ethyl acetate.
"EtOH" refers to ethanol.
"HATU" refers to O-(7-azabenzotriazol-1-yl)-1,1,3,3-tetramethyluromium hexafluorophosphate.
"HBTU" refers to 2-(1H-benzotriazol-1-yl)-1,1,3,3-tetramethyluronium hexafluorophosphate.
"HCl" refers to hydrochloric acid.
"HOAc" or "AcOH" refers to acetic acid.
"HOAt" or "HOAT" refers to 1-hydroxy-7-azabenzotriazole.
"HOBt" refers to 1-hydroxybenzotriazole monohydrate.
"i-BuOCOCl" refers to isobutylchloroformate.
"HPLC" refers to high pressure liquid chromatography.
"$LiAlH_4$" refers to lithium aluminum hydride.
"$LiAlH_2(OEt)_2$" refers to lithium aluminum hydride diethoxide.
"Me" refers to methyl.
"MeOH" refers to methanol.
"NMM" refers to N-methylmorpholine.
"NBS" refers to N-bromosuccinimide.
"$PhB(OH)_2$" refers to phenylboronic acid.
"$Ph_3P$" or "$PPh_3$" refers to triphenylphospine.
"PyBOP" refers to benzotriazole-ly-oxy-tris-pyrrolidino-phosphonium hexafluorophosphate.
"RP-HPLC" refers to reverse phase high pressure liquid chromatography.
"TFA" refers to trifluoroacetic acid.
"THF" refers to tetrahydrofuran.
"TLC" refers to thin layer chromatography.

BRIEF DESCRIPTION OF THE DRAWINGS

FIG. 8 depicts certain preferred compounds of the present invention.

FIG. 9 depicts other compounds of the present invention.

DETAILED DESCRIPTION OF THE INVENTION

1. Preferred Compounds

Figure 1:
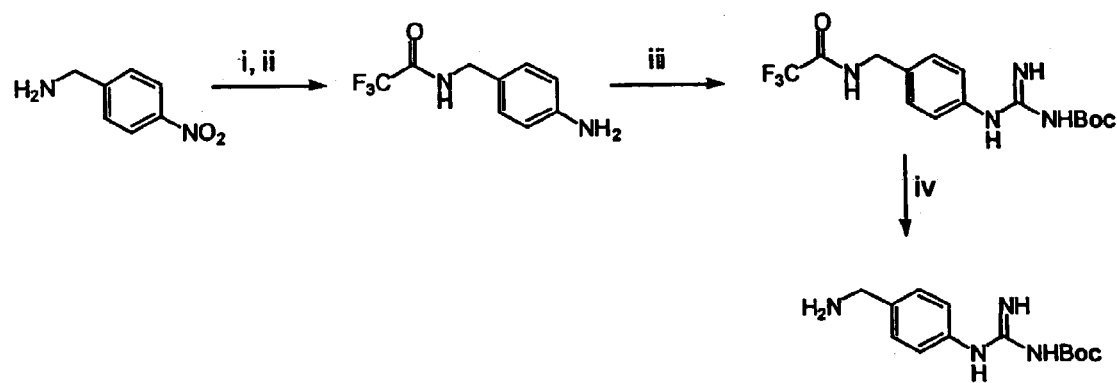
FIG. 1 depicts a reaction scheme for the synthesis of an intermediate used in the preparation of certain compounds of the present invention. In this figure, "i" through "iv" are defined as follows: i) trifluoracetic anhydride, 0° C., stir overnight; ice, $CH_2Cl_2$, $Na_2SO_4$; ii) Pd/C (10%) in MeOH (overnight); iii) N-N'-di-Boc-N"-trifluoromethanesulfonyl-guanidine, TEA, $CH_2Cl_2$, 6 hours, HCl, brine, $Na_2SO_4$; column chromatography ($CH_2Cl_2$/MeOH 99:1); and iv) potassium carbonate, $H_2O$/MeOH (2:15), overnight, $CH_2Cl_2$/MeOH (9:1), $Na_2SO_4$.

According to one aspect of the present invention, provided are compounds of formula (I) having urokinase inhibitory activity:

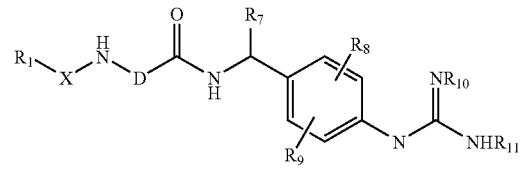

(a) X is selected from the group consisting of —S(O)$_2$—, —N(R')—S(O)$_2$—, —C(=O)—, —OC(=O)—, —NH—C(=O)—, —P(O)(R')—, and a direct link, wherein R' is independently hydrogen, alkyl of 1 to about 4 carbon atoms, aryl of about 6 to about 14 carbon atoms or aralkyl of about 7 to about 16 carbon atoms, with the proviso that when X is —P(O)(R')—, then R' is not hydrogen;

(b) $R_1$ is selected from the group consisting of:
(1) alkyl of 1 to about 12 carbon atoms which is unsubstituted or substituted with 1 or 2 substituents selected from the group consisting of $Y_1$ and $Y_2$,
(2) alkyl of 1 to about 3 carbon atoms substituted with cycloalkyl of about 3 to about 8 carbon atoms which is unsubstituted or substituted with 1 to 3 substituents selected from the group consisting of $Y_1$, $Y_2$, and $Y_3$,
(3) cycloalkyl of 3 to about 15 carbon atoms, which is unsubstituted or mono-, di-, or tri-substituted on the ring with 1 to 3 substituents selected from the group consisting of $Y_1$, $Y_2$, and $Y_3$,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is unsubstituted or mono-, di-, or tri-substituted on the ring with 1 to 3 substituents selected from the group consisting of $Y_1$, $Y_2$, and $Y_3$,
(5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, including,

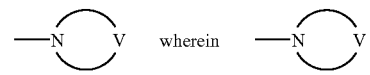

is a 5 to 7 member heterocycle having 3 to 6 ring carbon atoms, where V is —CH$_2$—, —O—, —S(=O)—, —S(O)$_2$— or —S—, which is unsubstituted or mono-, di-, or tri-substituted on the ring carbons with 1 to 3 substituents selected from the group consisting of $Y_1$, $Y_2$, and $Y_3$,
(6) alkenyl of 2 to about 6 carbon atoms which is unsubstituted or substituted with cycloalkyl of about 3 to about 8 carbon atoms, which is unsubstituted or mono-, di-, or tri-substituted on the ring with 1 to 3 substituents selected from the group consisting of $Y_1$, $Y_2$, and $Y_3$,
(7) aryl of about 6 to about 14 carbon atoms which is unsubstituted or mono-, di- or tri-substituted with 1 to 3 substituents selected from the group consisting of $Y_1$, $Y_2$, and $Y_3$,
(8) heteroaryl of about 5 to about 14 ring atoms with the ring atoms selected from carbon and heteroatoms, wherein the heteroatoms are selected from oxygen, nitrogen, and sulfur, and which is unsubstituted or mono-, di- or tri-substituted with 1 to 3 substituents selected from the group consisting of $Y_1$, $Y_2$, and $Y_3$, (9) aralkyl of about 7 to about 15 carbon atoms which is unsubstituted or substituted on the alkyl chain with hydroxy or halogen and which is unsubstituted or mono-, di-, or tri-substituted on the aryl ring with 1 to 3 substituents selected from the group consisting of $Y_1$, $Y_2$, and $Y_3$,

(10) heteroaralkyl of about 5 to about 14 ring atoms with the ring atoms selected from carbon and heteroatoms, wherein the heteroatoms are selected from oxygen, nitrogen, and sulfur, which is unsubstituted or substituted on the alkyl chain with hydroxy or halogen and which is unsubstituted on the ring or mono-, di- or tri-substituted on the ring with 1 to 3 substituents selected from the group consisting of $Y_1$, $Y_2$, and $Y_3$,

(11) aralkenyl of about 8 to about 16 carbon atoms which is unsubstituted or mono-, di-, or tri-substituted on the aryl ring with 1 to 3 substituents selected from the group consisting of $Y_1$, $Y_2$, and $Y_3$,

(12) heteroaralkenyl of about 5 to about 14 ring atoms with the ring atoms selected from carbon and heteroatoms, wherein the heteroatoms are selected from oxygen, nitrogen, and sulfur, and which is unsubstituted or mono-, di- or tri-substituted on the ring carbons with 1 to 3 substituents selected from the group consisting of $Y_1$, $Y_2$, and $Y_3$,

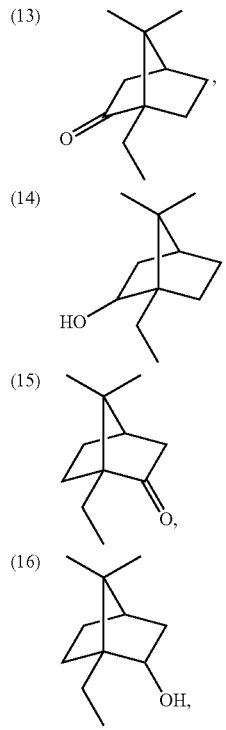

(17) fused carbocyclic alkyl of about 9 to about 15 carbon atoms,

(18) difluoromethyl or perfluoroalkyl of 1 to about 12 carbon atoms,

(19) perfluoroaryl of about 6 to about 14 carbon atoms,

(20) perfluoroaralkyl of about 7 to about 15 carbon atoms, and

(21) hydrogen when X is a direct link;

wherein each $Y_1$, $Y_2$, and $Y_3$ is independently selected and is (i) selected from the group consisting of halogen, cyano, nitro, tetrazolyl, guanidino, amidino, methylguanidino, —$CF_3$, —$CF_2CF_3$, —$CH(CF_3)_2$, —$C(OH)(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —$OH$, —$NH_2$, —$NHZ_1$, —$NZ_1Z_2$, —$C(=NH)NH_2$, —$C(=NOH)NH_2$, —N-morpholino, and —$S(O)_m(CF_2)_qCF_3$, wherein m is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 ring atoms, aralkyl of about 7 to about 15 carbon atoms, and heteroaralkyl of about 5 to about 14 ring atoms, or (ii) $Y_1$ and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl of 1 to about 12 carbon atoms, aryl of about 6 to about 14 carbon atoms, heteroaryl of about 5 to about 14 ring atoms, aralkyl of about 7 to about 15 carbon atoms, and heteroaralkyl of about 5 to about 14 ring atoms;

(c) D is

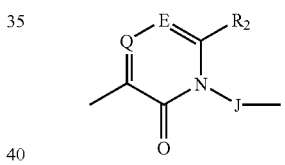

wherein (1) E is —N— or —$C(R_3)$—;
(2) Q is —N— or —$C(R_4)$—;
(3) $R_2$, $R_3$ and $R_4$ are independently selected and are selected from the group consisting of hydrogen, hydroxy, alkyl of 1 to about 8 carbon atoms, cycloalkyl of 3 to about 8 carbon atoms, alkoxy of 1 to about 8 carbon atoms, alkyl of 1 to about 8 carbon atoms substituted with hydroxy or —$NH_2$ trifluoromethyl, alkyl of 1 to about 8 carbon atoms substituted with cycloalkyl of 3 to about 8 carbon atoms, aralkyl of 7 to about 15 carbon atoms which is unsubstituted or substituted with 1 to 3 substituents independently selected from the group consisting of $Y_1$, $Y_2$ and $Y_3$; phenyl substituted with $Y_1$, a saturated 5 or 6-membered heterocyclic ring having 1 to 2 ring nitrogen atoms and the remainder of the ring atoms carbon atoms, —$NHR_5$, —$S(O)_tR_5$, and —$C(O)OR_5$; or $R_2$ is halogen;
(4) t is 0, 1 or 2;
(5) $R_5$ is selected from the group consisting of hydrogen, alkyl of 1 to about 6 carbon atoms, aryl of 6 to about 14 carbon atoms, which is unsubstituted or mono-, di-, or tri-substituted with 1 to 3 substituents selected from the group consisting of $Y_1$, $Y_2$ and $Y_3$; and aralkyl of about 7 to about 15 carbon atoms which is unsubstituted or substituted on the alkyl chain with hydroxy or halogen and which is unsubstituted or mono-, di- or tri-substituted on the aryl ring with 1 to 3 substituents selected from the group consisting of $Y_1$, $Y_2$ and $Y_3$;

(6) alternatively E is —C($R_3$)— and $R_2$ and $R_3$ are taken together to form a 5- or 6-membered aromatic ring which is unsubstituted or is substituted with $Y_1$;

(7) J is —C($R_{6a}$)($R_{6b}$)— wherein (i) $R_{6a}$ is in the S configuration and is selected from the group consisting of —$CH_3$, —$CH_2CH_3$, —$CH_2$—S—$CH_3$, —$CH_2OH$, —$CH_2CN$, —$CH_2C{\equiv}CH$, —$CH_2CH{=}CH_2$, and —$CH{=}CH_2$ and $R_{6b}$ is hydrogen; (ii) $R_{6a}$ and $R_{6b}$ are independently hydrogen or lower alkyl of 1 to about 3 carbon atoms; or (iii) $R_{6a}$ and $R_{6b}$ are selected together and are —$(CH_2)_k$— wherein k is 5 or 6 to give a spirocycloalkyl group; or (iv) J and $R_2$ are taken together as set forth in (8); and (8) alternatively J and $R_2$ selected together are

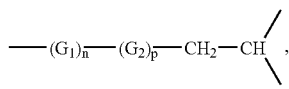

wherein $G_1$ and $G_2$ are independently —($CH_2$)— or a heteroatom selected from the group consisting of sulfur, oxygen and nitrogen, provided that $G_1$ and $G_2$ are not both heteroatoms, n is 0 or 1 and p is 0 or 1; to give D as

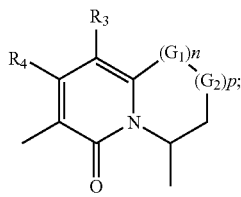

(d) $R_7$ is hydrogen or alkyl of 1 to about 4 carbon atoms;

(e) $R_8$ and $R_9$ are independently selected from the group consisting of hydrogen, hydroxy, halogen, alkyl of 1 to about 6 carbon atoms, alkyl of 1 to about 4 carbon atoms substituted with alkoxy of 1 to about 4 carbon atoms, alkoxy of 1 to about 6 carbon atoms, and trifluoromethyl;

(f) $R_{10}$ and $R_{11}$ are independently selected from the group consisting of hydrogen, hydroxy, alkoxy of 1 to about 3 carbon atoms, trihydrocarbylsilyl of 3 to about 16 carbon atoms, alkyl of 1 to about 3 carbon atoms and —C(=O)$R_{12}$ with the proviso that $R_{10}$ and $R_{11}$ are not both hydroxy or alkoxy; and $R_{12}$ is hydrogen, alkyl of 1 to about 6 carbon atoms, alkoxy of 1 to about 6 carbon atoms or —$(CF_2)_jCF_3$ wherein j is 0, 1, 2 or 3; with the proviso that, when Q is —N—, then X is not —S(O)$_2$—; and pharmaceutically acceptable salts thereof.

Preferred X groups include —S(O)$_2$—, —C(=O)—, —NH—C(=O)—, —OC(=O)—, and a direct link. Particularly preferred X groups include —S(O)$_2$—.

Preferred $R_1$ groups include aralkyl, substituted aralkyl, aryl, substituted aryl, alkyl, substituted alkyl and alkyl substituted with optionally substituted cyclocalkyl. According to one aspect of the present invention, particularly preferred $R_1$ substituents include substituted or unsubstituted benzyl and substituted or unsubstituted phenyl, especially preferred ring substitutions include para substitutions.

Exemplary $R_1$ groups include alkyl groups, especially isobutyl, 2-ethylhexyl, methyl, n-butyl, isopropyl, cyclohexylmethyl, and cyclohexylpropyl; cycloalkyl groups, especially (−)menthyl, (+)menthyl, and cyclohexyl; aryl groups, such as naphthyl and phenyl; aralkyl groups, such as benzyl, substituted benzyl, 3-phenylpropyl, and 2-phenylethyl; and fused carbocyclic alkyls, such as fluorenylmethyl. Especially preferred $R_1$ groups include phenyl, benzyl, para-substituted benzyl, 2-phenylethyl, isobutyl, n-butyl and 3-phenylpropyl.

Preferred combinations of $R_1$—X— include phenyl-S(O)$_2$—, benzyl-S(O)$_2$—, 4-iodo-benzyl-S(O)$_2$—, 2-phenylethyl-S(O)$_2$—, 3-phenylpropyl-S(O)$_2$—, n-butyl-S(O)$_2$—, benzyl-C(=O)—, and isobutyl-C(=O)—.

Preferred D groups include those where E is —C($R_3$)— and Q is —C($R_4$)—. More preferably $R_3$ is hydrogen and $R_4$ is hydrogen or methyl.

Preferred $R_2$ groups include hydrogen.

Preferred compounds where J is —C($R_{6a}$)($R_{6b}$)— include those where $R_{6a}$ is alkyl, more preferably methyl, and $R_{6b}$ is hydrogen. More preferably $R_{6a}$ is in the S-configuration to give an L-amino acid residue. When $R_{6a}$ is in the S-configuration, $R_{6a}$ is preferably methyl or ethyl. Also preferred are compounds where $R_2$ and J selected together are

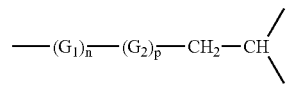

to give a ring of the formula:

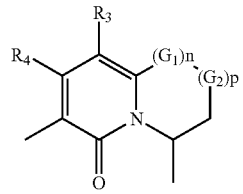

Preferably n is 0 and p is 1. More preferably $G_2$ is —$CH_2$— or a heteroatom, preferred heteroatoms include sulfur.

Preferred $R_7$ groups include hydrogen.

Preferred $R_8$ and $R_9$ groups include hydrogen.

Preferred $R_{10}$ and $R_{11}$ groups include hydrogen.

According to one aspect of the present invention, provided are compounds wherein J is —C($R_{6a}$)($R_{6b}$)—. Preferred compounds according to this aspect include those wherein $R_{6a}$ is in the S-configuration and $R_{6b}$ is hydrogen (to give an L-amino acid residue).

According to an alternate aspect of this invention, provided are compounds wherein E is —C($R_3$)— and Q is —C($R_4$)—. According to a first embodiment of this aspect, J is —C($R_{6a}$)($R_{6b}$)—. According to a second embodiment of this aspect, $R_2$ and J taken together are

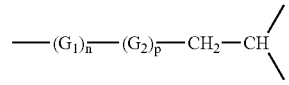

to give

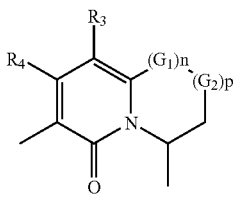

(II)

According to this aspect, $R_3$ is preferably hydrogen and $R_4$ is preferably hydrogen or alkyl, more preferable hydrogen or methyl. According to an embodiment of this aspect, preferred are compounds wherein X is —S(O)$_2$—, —C(=O)—, —NH—C(=O)— or a direct link. When X is —S(O)$_2$—, $R_1$ is preferably benzyl or substituted benzyl. Preferred substituted benzyl groups included those having a para substitution. Other preferred $R_1$ groups include straight chain or branched alkyl groups which are optionally substituted or alkyl of 1 to about 3 carbon atoms substituted with optionally substituted cycloalkyl. According to an embodiment of this aspect, $R_2$ and J form a bicyclic group of formula II as set forth hereinabove having the l(S) configuration.

Preferred compounds of the present invention include those depicted in FIGS. 8 and 9. Especially preferred are Compounds A to F of FIG. 8.

2. Preparation of Preferred Compounds

FIG. 1 depicts a reaction scheme for the synthesis of an intermediate used in the preparation of compounds of the present invention having a 4-guanidinophenyl at P1.

Figure 2:
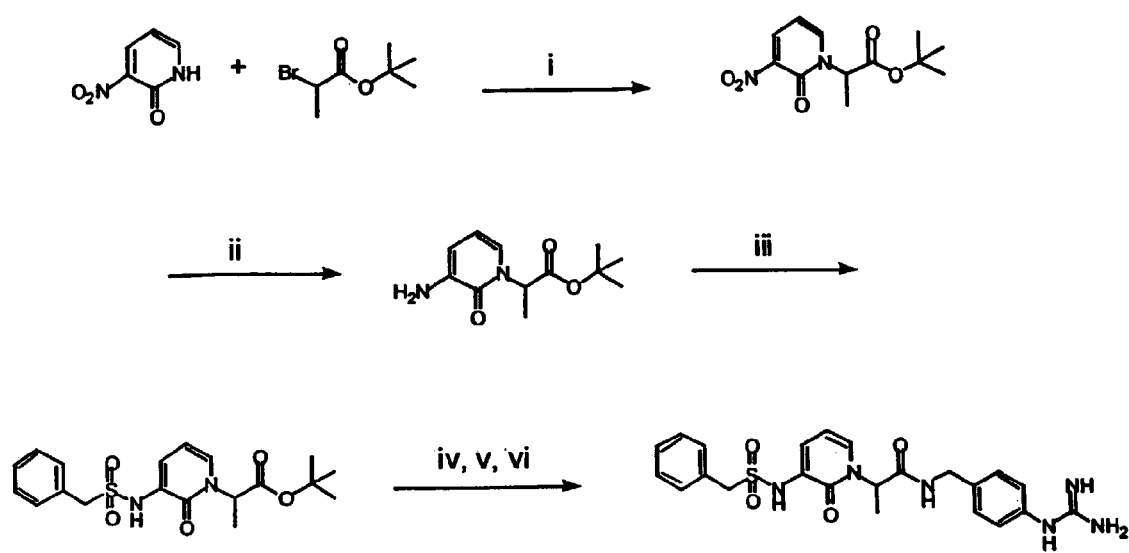
FIG. 2 depicts a reaction scheme for the synthesis of a compound of the present invention. In this figure, "i" through "vi" are defined as follows: i) NaH (60% in oil), DMF; ii) PdOH/C (15%), $H_2$ (40 psi), quantitative yield; iii) $BnSO_2Cl$, TEA, AcN, 85% yield; iv) TFA, $CH_2Cl_2$; v) N-[(4-aminomethyl)phenyl]-N'-tert-butoxycarbonyl guanidine, HATU, DIEA, $CH_3CN$; and vi) TFA, $CH_2Cl_2$.
Figure 3:
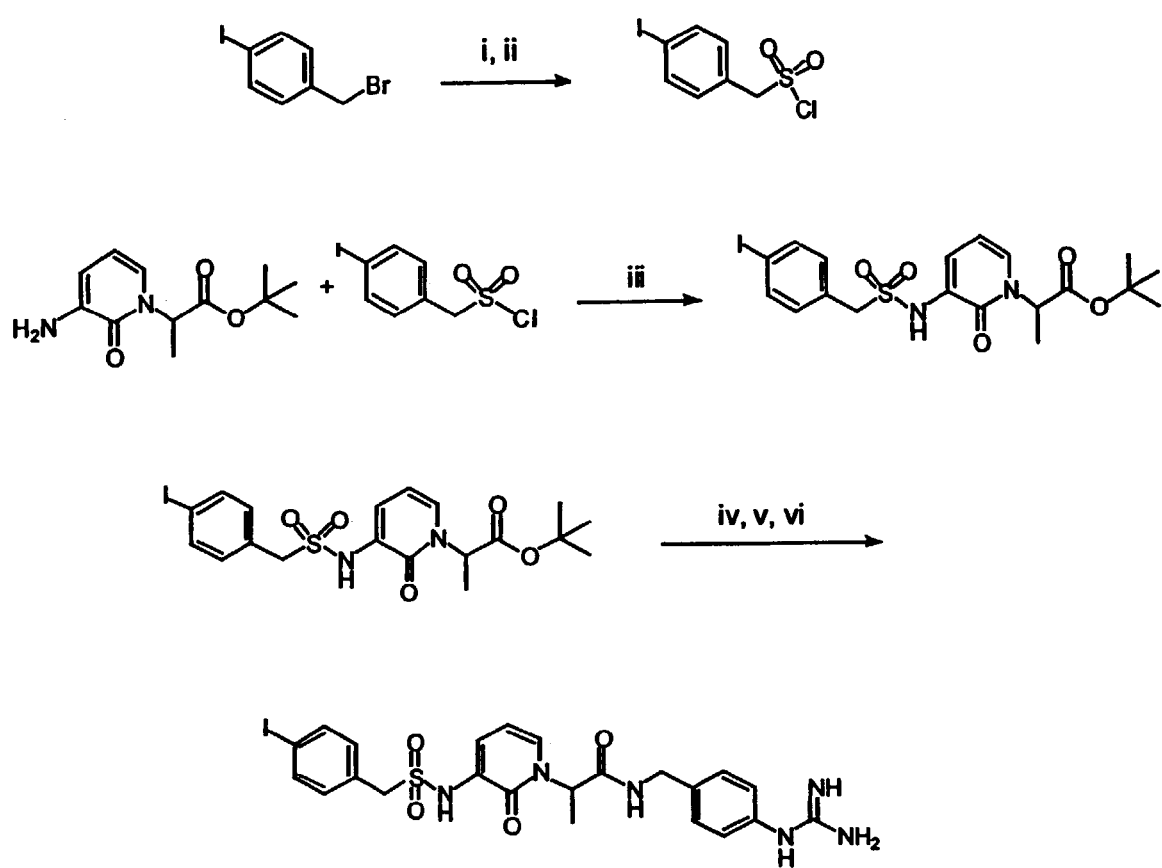
FIG. 3 depicts a reaction scheme for the synthesis of a compound of the present invention. In this figure, "i" through "vi" are defined as follows: i) thiourea, MeOH; ii) $Cl_2(g)$, $H_2O$/1,4-dioxane; iii) TEA, $CH_2CN$; iv) TFA, $CH_2Cl_2$; v) N[(4-aminomethyl)phenyl]-N'-tert-butoxycarbonyl guanidine (product of Example 3), HATU, DIEA, $CH_3CN$; and vi) TFA, $CH_2Cl_2$.
Figure 4:
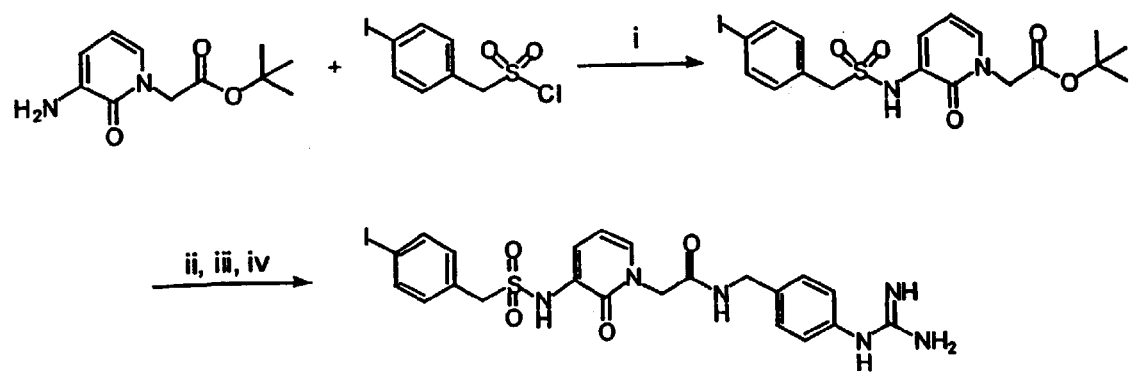
FIG. 4 depicts a reaction scheme for the synthesis of a compound of the present invention. In this figure, "i" through "iv" are defined as follows: i) TEA, $CH_3CN$; ii) TFA, $CH_2Cl_2$; iii) N-[(4-aminomethyl)phenyl]-N'-tert-butoxycarbonyl guanidine (product of Example 3), HATU, DIEA, $CH_3CN$; and iv) TFA, $CH_2Cl_2$.

FIGS. 2 to 4 depict reaction schemes for the synthesis of certain compounds of the present invention.

Figure 5A:
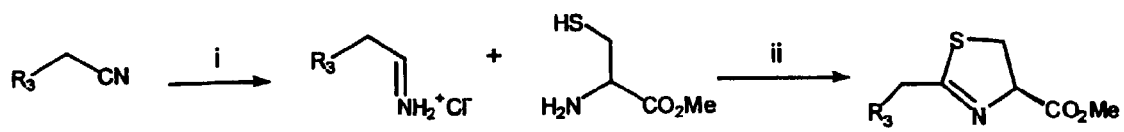
FIGS. 5A to 5C depict reaction schemes for the synthesis of certain compounds of the present invention. In these figures, "i" through "vi" are defined as follows: i) HCl(g), EtOH; ii) TEA, $CH_2Cl_2$; iii) $R_4COCl$, DMAP; iv) dry HCl(g), DCE, reflux; v) $HNO_3$, acetic anhydride, −12° C.; and vi) $H_2$/Pd/C.
Figure 5B:
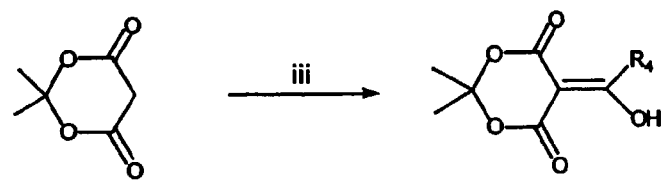
Figure 5C:
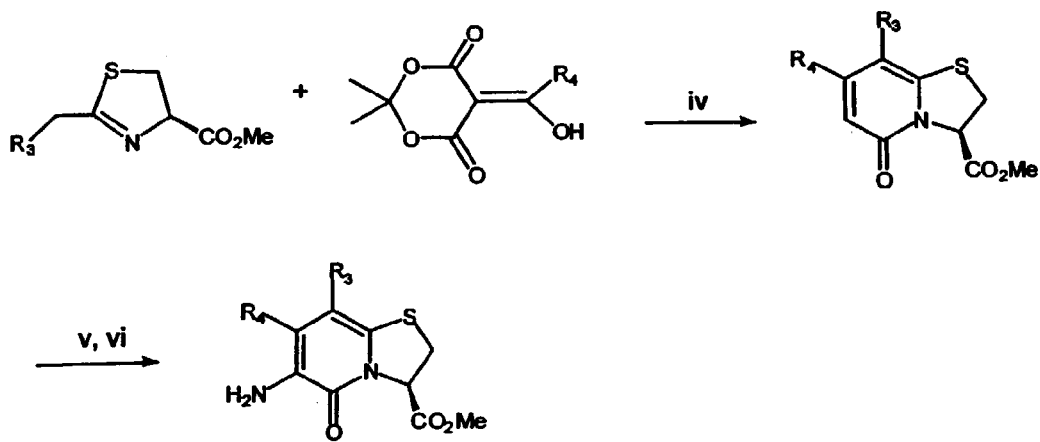

FIGS. 5A to 5C depict reaction schemes for the synthesis of intermediates which may be used in the synthesis of compounds of the present invention.

Figure 6:
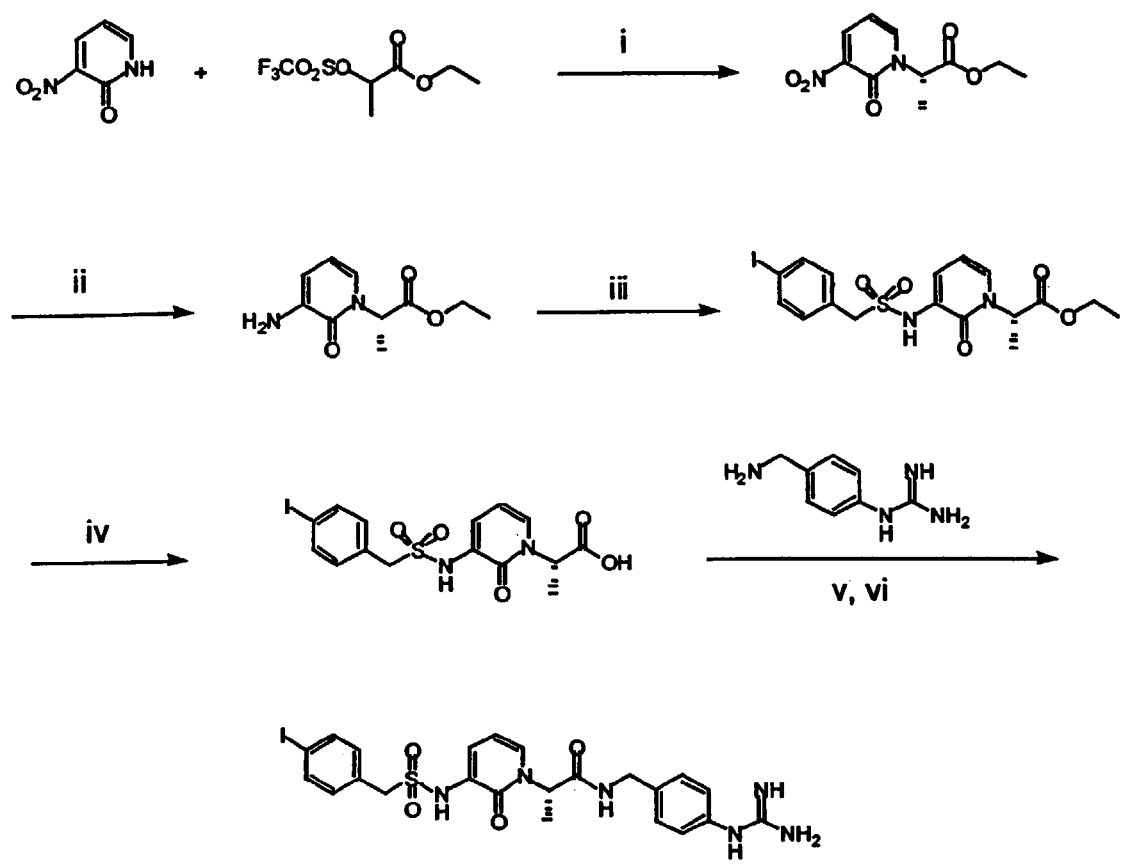
FIG. 6 depicts a reaction scheme for the synthesis of a compound of the present invention. In this figure, "i" through "vi" are defined as follows: (i) NaH (60% in oil), DMF; (ii) PdOH/C (15%), $H_2$(30 psi), MeOH; (iii) 4-iodobenzylsulfonylchloride, TEA, AcN; (iv) LiOH, dioxane/$H_2O$(4:1); (v) HATU, HOAT, DIEA, $CH_3CN$; and (vi) $CH_2Cl_2$/TFA.

FIG. 6 depicts a reaction scheme for the stereospecific synthesis of a compound of the present invention.

Figure 7:
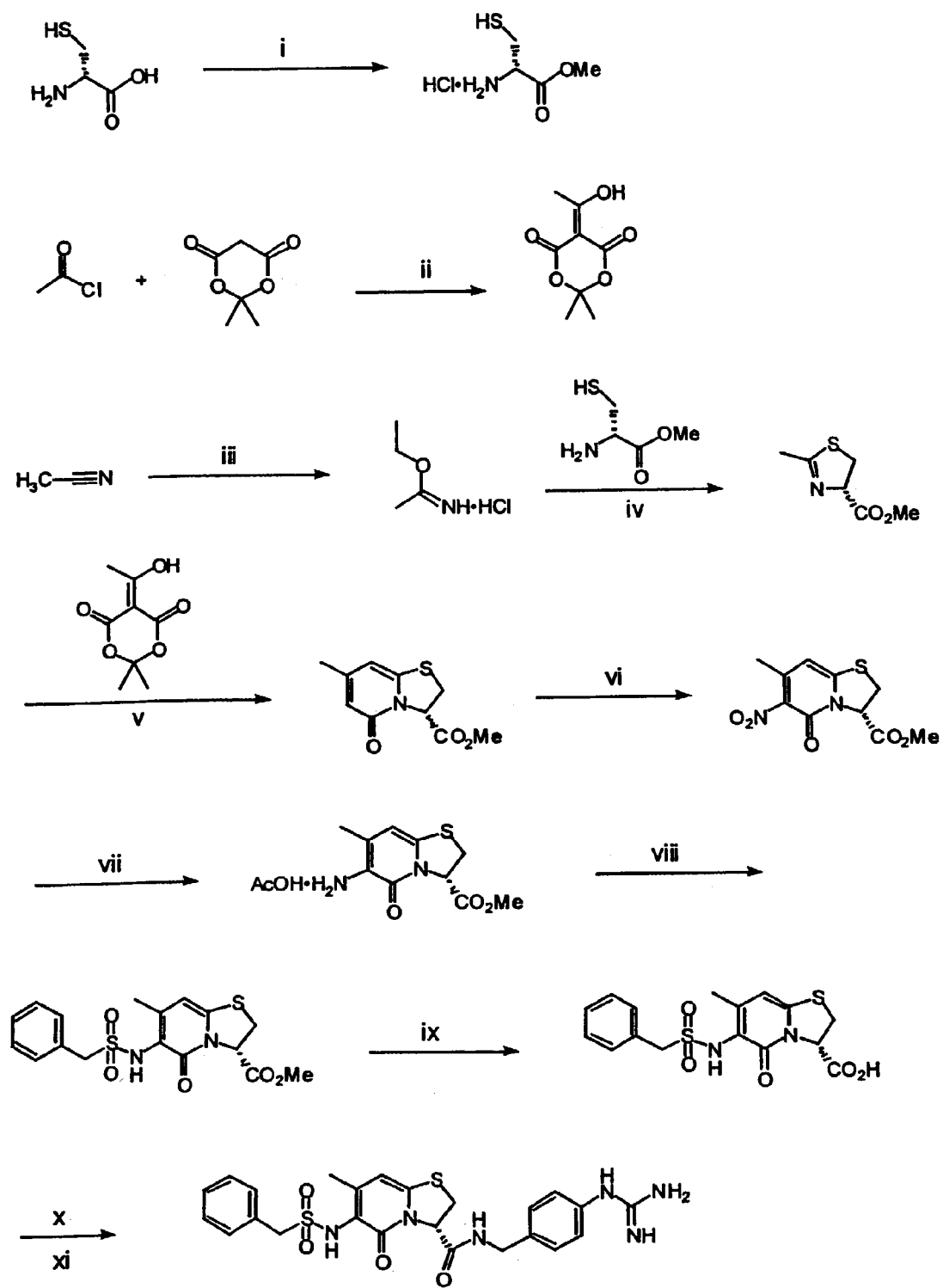
FIG. 7 depicts a reaction scheme for the synthesis of a compound of the present invention. In this figure, "i" through "xi" are defined as follows: (i) anhydrous methanol, anhydrous HCl(g), reflux; (ii) DMAP, DCM; (iii) anhydrous HCl(g), absolute ethanol, 0° C., four hours; (iv) DCM, TEA; (v) HCl(g), product of Example 34, DCE; (vi) $HNO_3$, $Ac_2O$, −12° C.; (vii) Fe (powder), AcOH; (viii) $BnSO_2Cl$, TEA, DCM; (ix) LiOH, dioxane; (x) product of Example 3, HOAt, HATU, DIEA, AcN; and (xi) TFA, DCM.

FIG. 7 depicts a reaction scheme for the synthesis of a compound of the present invention wherein D is a fused bicyclic heterocyclic group.

Published PCT application WO 01/36426 describes the synthesis of certain bicyclic pyridinone derivatives which may be used as intermediates for the synthesis of compounds of the present invention.

Preferred means of chemically coupling (as for example, amide bond function) include formation of a peptide bond by using conventional coupling reagents known in the art. See Bodanszky, N. *Peptide Chemistry*, pp. 55-73, Springer-Verlag, New York (1988) and references cited therein. The chemical coupling may be either by means of one-step or two-step coupling. In one-step coupling, the two coupling partners are coupled directly. Preferred coupling reagents for one-step coupling of the coupling partners include DCC with HOBt, EDC with HOBt, EDC with HOAt, HBTU or TBTU. In two-step coupling, an activated ester or anhydride of the C-terminal carboxy group of one coupling partner is formed prior to its coupling to the other coupling partner.

For preparation of certain compounds having hydrogenation-sensitive substituent groups, it is preferred to avoid the use of hydrogen gas with palladium on carbon. Another preferred method for preparing compounds of the present invention containing hydrogenation sensitive groups such as alkenyl or aryl moieties substituted with halogen, cyano, nitro, or —S-$Z_1$, is to use boron tris(trifluoroacetate), B(OCOCF$_3$)$_3$, to cleave the N$^g$-nitro of the arginine group. The reagent is prepared by the reaction of BBr$_3$ and CF$_3$COOH in dichloromethane at 0° C. The reagent is also commercially available. Generally, the N$^g$-nitro compound is treated with boron tris(trifluoroacetate) in trifluoroacetic acid at 0° C. See, e.g., Fieser, M. and Fieser, L. F., *Reagents for Organic Synthesis*, p. 46, John Wiley & Sons, New York (1974); Pless, J., and Bauer, W. *Angew. Chem., Internat. Ed.*, 12, 147 (1973).

In addition, another preferred reagent for selective nitro group cleavage is titanium trichloride. This reagent is commercially available. The N$^g$ nitro compound is treated with titanium trichloride in aqueous methanol containing an ammonium acetate buffer followed by exposure of the reaction mixture to air or dimethyl sulfoxide. See, e.g., Freidinger, R. M., Hirschmann, R., and Veber, D. F., *J. Org. Chem.*, 43, 4800 (1978).

3. Selection of Preferred Compounds

According to one aspect of the present invention, preferred compounds of the present invention are selected for their potency and selectivity toward inhibition of serine proteases, especially urokinase. Such evaluations are routinely performed in vitro, following procedures such as those set forth in Example A. As described therein, and as generally known, a target serine protease and its substrate are combined under assay conditions permitting reaction of the protease with its substrate. The assay is performed in the absence of test compound, and in the presence of increasing concentrations of the test compound. The concentration of test compound at which 50% of the serine protease activity is inhibited by the test compound is the IC$_{50}$ value (Inhibitory Concentration) or EC$_{50}$ (Effective Concentration) value for that compound. Within a series or group of test compounds, those having lower IC$_{50}$ or EC$_{50}$ values are considered more potent inhibitors of the serine protease than those compounds having higher IC$_{50}$ or EC$_{50}$ values. The IC$_{50}$ measurement is often used for more simplistic assays, whereas the EC$_{50}$ is often used for more complicated assays, such as those employing cells. K$_i$ is calculated from the IC$_{50}$.

Preferred compounds according to this aspect of the present invention have a K$_i$ value of 100 nM or less as measured in an in vitro assay for inhibition of urokinase activity. Especially preferred compounds have a K$_i$ value of less than 30 nM.

The test compounds also are evaluated for selectivity toward a serine protease. As described in the Examples, and as generally known, a test compound is assayed for its potency toward a panel of serine proteases and other enzymes and an IC$_{50}$ value or EC$_{50}$ value is determined for each test compound in each assay system. A compound that demonstrates a low IC$_{50}$ value or EC$_{50}$ value or corresponding low K$_i$ value for the target enzyme, e.g., urokinase, and a higher IC$_{50}$ value or EC$_{50}$ value for other enzymes within the test panel (e.g., tissue plasminogen activator, thrombin, Factor Xa), is considered to be selective toward the target enzyme. Generally, a compound is deemed selective if its IC$_{50}$ value or EC$_{50}$ value (or K$_i$ value) in the target enzyme assay is at least one order of magnitude less than the next smallest IC$_{50}$ value or EC$_{50}$ value measured in the selectivity panel of enzymes.

Preferred compounds of the present invention have a K$_i$ value of 100 nM or less as measured in an in vitro assay for inhibition of urokinase activity. Especially preferred compounds have a K$_i$ value in the in vitro urokinase inhibition assay that is at least one order of magnitude smaller than the IC$_{50}$ value measured in the in vitro tPA inhibition assay.

Compounds having a selectivity ratio of $IC_{50}$ tPA assay: $K_i$ urokinase assay of greater than 100 are especially preferred.

Compounds of the present invention also are evaluated for their activity in vivo. The type of assay chosen for evaluation of test compounds will depend on the pathological condition to be treated or prevented by use of the compound, as well as the route of administration to be evaluated for the test compound.

For instance, to evaluate the activity of a compound of the present invention to reduce tumor growth through inhibition of urokinase, the procedures described by Jankun et al. [Canc. Res. 57:559-563, 1997] to evaluate PAI-1 can be employed. Briefly, the ATCC cell lines DU145, which expresses a high level of uPA, and LnCaP, which does not express uPA, are injected into SCID mice. After tumors are established, the mice are given test compound according to a dosing regime determined from the compound's in vitro characteristics. The Jankun et al. compound was administered in water. Tumor volume measurements are taken twice a week for about five weeks. A compound is deemed active if an animal to which the compound was administered exhibited decreased tumor volume, as compared to animals receiving appropriate control compounds. Furthermore, a comparison of a compound's effect in animals injected with DU145 cells versus LnCaP cells can indicate whether the compound's effect was due to inhibition of urokinase or otherwise.

Another in vivo experimental model designed to evaluate the effect of p-aminobenzamidine, a purported urokinase inhibitory compound, on reducing tumor volume is described by Billström et al. [Int. J. Cancer 61:542-547, 1995].

To evaluate the ability of a compound of the present invention to reduce the occurrence of, or inhibit, metastasis, the procedures described by Kobayashi et al. [Int. J. Canc. 57:727-733d, 1994] can be employed. Briefly, a murine xenograft selected for high lung colonization potential is injected into C57B1/6 mice i.v. (experimental metastasis) or s.c. into the abdominal wall (spontaneous metastasis). Various concentrations of the compound to be tested can be admixed with the tumor cells in Matrigel prior to injection. Daily i.p. injections of the test compound are made either on days 1-6 or days 7-13 after tumor inoculation. The animals are killed about three or four weeks after tumor inoculation, and the lung tumor colonies are counted. Evaluation of the resulting data permits a determination as to efficacy of the test compound, optimal dosing and route of administration.

The activity of the compounds of the present invention toward decreasing tumor volume and metastasis can be evaluated in the model described by Rabbani et al. [Int. J. Cancer 63:840-845, 1995] to evaluate their inhibitor. There, Mat LyLu tumor cells over-expressing uPA were injected into the flank of Copenhagen rats. The animals were implanted with osmotic minipumps to continuously administer various doses of test compound for up to three weeks. The tumor mass and volume of experimental and control animals were evaluated during the experiment, as were metastatic growths. Evaluation of the resulting data permits a determination as to efficacy of the test compound, optimal dosing, and route of administration. Some of these authors described a related protocol in Xing et al. [Canc. Res. 57:3585-3593, 1997].

To evaluate the inhibitory activity of a compound of the present invention toward neovascularization, a rabbit cornea neovascularization model can be employed. Avery et al. [Arch. Ophthalmol. 108:1474-1475, 1990] describe anesthetizing New Zealand albino rabbits and then making a central corneal incision and forming a radial corneal pocket. A slow release prostaglandin pellet was placed in the pocket to induce neovascularization. Test compound was administered i.p. for five days, at which time the animals were killed. The effect of the test compound is evaluated by review of periodic photographs taken of the limbus, which can be used to calculate the area of neovascular response and, therefore, limbal neovascularization. A decreased area of neovascularization as compared with appropriate controls indicates the test compound was effective at decreasing or inhibiting neovascularatization.

An angiogenesis model used to evaluate the effect of a test compound in preventing angiogenesis is described by Min et al. [Canc. Res. 56:2428-2433, 1996]. C57BL6 mice receive subcutaneous injections of a Matrigel mixture containing bFGF, as the angiogenesis-inducing agent, with and without test compound. After five days, the animals are killed and the Matrigel plugs, in which neovascularization can be visualized, are photographed. An experimental animal receiving Matrigel and an effective dose of test compound will exhibit less vascularization than a control animal or an experimental animal receiving a less- or non-effective dose of compound.

An in vivo system designed to test compounds for their ability to limit the spread of primary tumors is described by Crowley et al. [Proc. Natl. Acad. Sci. 90:5021-5025, 1993]. Nude mice are injected with tumor cells (PC3) engineered to express CAT (chloramphenicol acetyltransferase). The cells secrete large amounts of uPA and exhibit saturating amounts of uPA activity bound to uPAR on the cell surface. Compounds to be tested for their ability to decrease tumor size and/or metastases are administered to the animals, and subsequent measurements of tumor size and/or metastatic growths are made. In addition, the level of CAT detected in various organs provides an indication of the ability of the test compound to inhibit metastasis; detection of less CAT in tissues of a treated animal versus a control animal indicates less CAT-expressing cells migrated to that tissue.

In vivo experimental models designed to evaluate the urokinase inhibitory potential of a test compound, using a tumor cell line F3II, said to be highly invasive, are described by Alonso et al. [Breast Canc. Res. Treat. 40:209-223, 1996]. This group describes in vivo studies for toxicity determination, tumor growth, invasiveness, spontaneous metastasis, experimental lung metastasis, and an angiogenesis assay.

The CAM model (chick embryo chorioallantoic membrane model), first described by L. Ossowski in 1998 [J. Cell Biol. 107:2437-2445, 1988], provides another method for evaluating the urokinase inhibitory activity of a test compound. In the CAM model, invasion of tumor cells through the chorioallantoic membrane is dependent upon the presence of catalytically active uPA. Contacting CAM with tumor cells in the presence of a urokinase inhibitory agent, results in less or no invasion of the tumor cells through the membrane. Thus, the CAM assay is performed with CAM and tumor cells in the presence and absence of various concentrations of test compound. The invasiveness of tumor cells is measured under such conditions to provide an indication of the compound's urokinase inhibitory activity. A compound having urokinase inhibitory activity correlates with less tumor invasion.

The CAM model is also used in a standard assay of angiogenesis (i.e., effect on formation of new blood vessels (Brooks, P. C.; Montgomery, A. M. P.; and Cheresh, D. A., Methods in Molecular Biology 129: 257-269 (1999)). According to this model, a filter disc containing an angiogenesis inducer, such as basic fibroblast growth factor (bFGF) is placed onto the CAM. Diffusion of the cytokine into the CAM induces local angiogenesis, which may be measured in several ways such as by counting the number of blood vessel branch points within the CAM directly below the filter disc. The ability of compounds of the present invention to inhibit cytokine-induced angiogenesis can be tested using this model. A test compound can either be added to the filter disc that contains the angiogenesis inducer, be placed directly on the membrane or be administered systemically. The extent of new blood vessel formation in the presence and/or absence of test compound can be compared using this model. The formation of fewer new blood vessels in the presence of a test compound would be indicative of anti-angiogenesis activity. Since certain of the compounds of the present invention are active as inhibitors of urokinase, anti-angiogenesis activity for such compounds may suggest that urokinase plays a significant role in angiogenesis.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

5. Utility

The compounds of the present invention having urokinase inhibitory activity and/or activity in reducing or inhibiting blood vessel formation, including angiogenesis and neovascularization, may be used both in vitro and in vivo for a number of applications, some of which are described herein below.

The compounds of the present invention are active as inhibitors of urokinase and specifically bind urokinase. Accordingly those compounds that contain sites suitable for linking to a solid/gel support may be used in vitro for affinity chromatography to purify urokinase from a sample or to remove urokinase from a sample using conventional affinity chromatography procedures. These compounds are attached or coupled to an affinity chromatography either directly or through a suitable linker support using conventional methods. See, e.g. Current Protocols in Protein Science, John Wiley & Sons (J. E. Coligan et al., eds, 1997) and Protein Purification Protocols, Humana Press (S. Doonan, ed., 1966) and references therein.

The compounds of the present invention having urokinase inhibitory activity are useful in in vitro assays to measure tPA activity in a sample. In assays which measure the total plasminogen activation activity in a blood sample, a compound of the present invention having urokinase inhibiting activity will knock out that portion of plasminogen activation attributable to uPA, which will allow for calculation of the portion of the total plasminogen activation due to tPA activity as well as that due to uPA activity. Use of such assays to monitor tPA activity would allow better dosage control in patients receiving tPA. These assays could also be used to monitor uPA activity levels in tissue samples, such as from biopsy or to monitor uPA/tPA activities for any clinical situation where measurement of plasminogen activation activity is of assistance. These assays may also be used to monitor plasminogen activator activity where a patient has been treated with a non-endogenous compound having plasminogen activator activity, such as streptokinase and staphlyokinase.

The compounds of the present invention are useful in vivo for treatment of pathologic conditions which would be ameliorated by decreased urokinase activity. For example these compounds will inhibit the activation of metalloproteases by the uPA-plasmin cascade in synovial fluid and thus, may be used in treatment of arthritis.

It is believed these compounds will be useful in decreasing or inhibiting metastasis, neovascularization, and degradation of the extracellular matrix in tumors and other neoplasms. These compounds will be useful as therapeutic agents in treating conditions characterized by pathological neovascularation such as retinal disease, retinopathies and other conditions, including those described hereinabove in the Background and Introduction to the Invention.

Another use for the compounds of the present invention having urokinase inhibitory activity is as an antidote if too much exogenous urokinase has been given to a patient for therapeutic purposes, such as for dissolving a blood clot.

The compounds of the present invention may be used in treating conditions characterized by inflammation due to their anti-inflammatory effects from inhibition of urokinase, thereby interfering with mediators of cell adhesion or migration. Such anti-inflammatory applications include treatment of stroke and complications of organ transplants.

The present invention includes methods for preventing or treating a condition in a mammal suspected of having a condition which will be attenuated by inhibition of urokinase activity comprising administering to said mammal a therapeutically effective amount of a compound or a pharmaceutical composition of the present invention.

These compounds or pharmaceutical compositions are typically administered to a mammal in need thereof for a time and under conditions effective to have the intended therapeutic effect (such as inhibiting urokinase, inhibiting or decreasing angiogenesis or inhibiting or decreasing tumor cell growth.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably oral, such as by tablets capsules or elixirs taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a "therapeutically effective amount" of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of inhibiting uPA activity, will be within the ambit of one skilled in these arts. Typically, administration of the compounds or pharmaceutical composition of the present invention is commenced at lower dosage levels, with dosage levels being increased until the desired effect of inhibiting uPA activity to the desired extent is achieved, which would define a therapeutically effective amount. For the compounds of the present invention, alone or as part of a pharmaceutical composition, such doses are between about 0.01 mg/kg and 100 mg/kg body weight, preferably between about 0.01 mg/kg and 10 mg/kg, body weight.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Preparation of

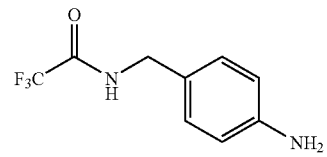

4-Nitrobenzylamine (4.0 g, 21 mmol) was added in portions to trifluoroacetic anhydride (15 mL) while the mixture was being cooled on ice. The mixture was allowed to warm to room temperature and stirred overnight. The suspension was poured onto ice (approximately 200 g), and the cloudy suspension was extracted with $CH_2Cl_2$ (2×100 mL), dried over $Na_2SO_4$ and the solvent removed to give a transparent oil. This oil was shaken in a Parr flask with Pd/C (10%, 300 mg) in MeOH (50 mL) overnight. The solid was removed by filtration and the solvent removed in vacuo to give a white solid corresponding to the product compound (4.5 g, quantitative yield).

Example 2

Preparation of

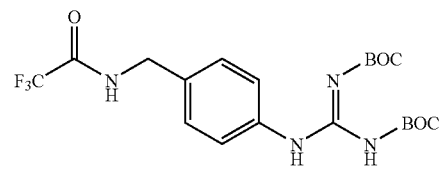

The product of Example 1 (279 mg, 1.28 mmol) was added to a stirring mixture of N-N'-Di-Boc-N"-trifluoromethanesulfonyl-guanidine (prepared according to the procedure described in J. Org. Chem. 1998, 63, 3804-3805) (500 mg, 1.28 mmol), TEA (108 µL, 1.28 mmol) in $CH_2Cl_2$ (10 mL). The reaction mixture was stirred for 6 hours. The mixture was diluted with $CH_2Cl_2$ (30 mL) and washed with HCl (1M, 20 mL), brine (20 mL), dried over $Na_2SO_4$ and the solvent removed in vacuo to give a solid. Column chromatography ($CH_2Cl_2$/MeOH, 99:1) gave a white solid corresponding to the product compound (350 mg, 52%).

Example 3

Preparation of

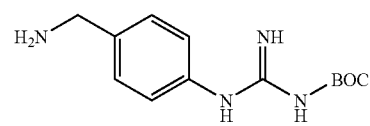

Potassium carbonate (500 mg) was added to a stirring solution of the product of Example 2 (300 mg, 0.833 mmol) in $H_2O$/MeOH (2:15, 17 mL) and the mixture was stirred overnight. The solvent was removed in vacuo, and the remaining residue was dissolved in H₂O (10 mL) and extracted with CH₂Cl₂/MeOH (9:1, 3×10 mL). The organic layers were dried over Na₂SO₄ and removed in vacuo to give a white solid corresponding to the product compound (150 mg, 68%).

Example 4

Preparation of

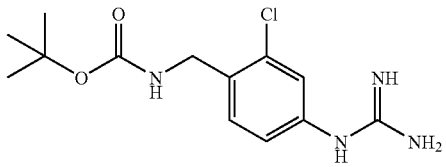

(4-Amino-2-chloro-benzyl)-carbamic acid tert-butyl ester (250 mg, 0.978 mmol), was added to a stirring mixture of N-N'-bis-Boc-N''-trifluoromethanesulfonyl-guanidine (343 mg, 0.879 mmol), and TEA (108 μL, 1.28 mmol) in CH₂Cl₂ (5 mL). The mixture was stirred for 24 hours. The mixture was diluted with CH₂Cl₂ (20 mL) and washed with HCl (1M, 20 mL), brine (10 mL). The organic layer was dried over Na₂SO₄. The solvent was removed in vacuo to give a solid. Column chromatography (CH₂Cl₂/MeOH, 99:1) gave an oil corresponding to the product compound (150 mg, 34%).

Example 5

Preparation of

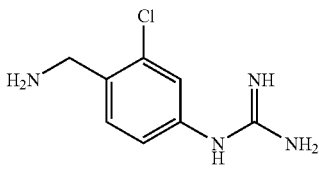

A solution of the product of Example 4 (100 mg, 0.201 mmol) in a mixture of CH₂Cl₂/TFA (1:1, 2 mL) was stirred at room temperature for 90 minutes. The solvent was removed in vacuo to give a transparent oil.

Example 6

Preparation of

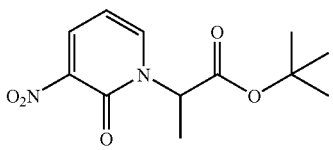

NaH (60% in oil, 943 mg, 24 mmol) was added in portions (over 5 minutes) to a stirring solution of 2-hydroxy-3-nitropyridine (3.0 g, 21 mmol) in DMF (30 mL). After 30 minutes, 2-bromopropionic acid tert-butylester (3.48 mL) was added. The mixture was stirred overnight and the solvent was removed in vacuo. Column chromatography (CH₂Cl₂/MeOH, 99:1) gave the title compound as yellow solid (4.5 g, 80%), MS (electrospray) 269 (M+1).

Example 7

Preparation of

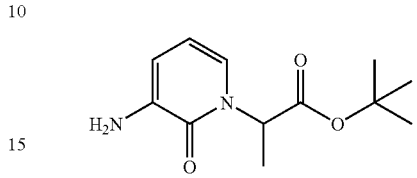

A solution of the product of Example 6 (2.0 g, 1.87 mmol), PdOH (15% on carbon, 200 mg) in MeOH (10 mL) was shaken under H₂ (40 psi) for 3 hours. The catalyst was removed by filtration and the solvent removed in vacuo to give an oil corresponding to the title compound, MS (electrospray) 239 (M+1).

Example 8

Preparation of

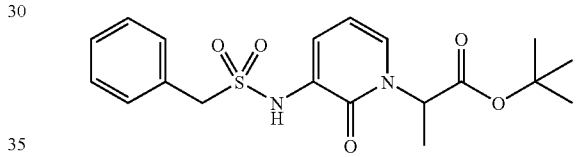

A solution of the product of Example 7 (500 mg, 1.87 mmol), benzylsulfonylchloride (356 mg, 1.87 mmol), and TEA (807 μL, 5.60 mmol) in acetonitrile (10 mL) was stirred at room temperature overnight. The solvent was removed in vacuo and the residual oil was diluted with water (20 mL). The water layer was extracted with CH₂Cl₂ (3×50 mL) and the combined organic layers were dried over Na₂SO₄. Solvent was removed to give a yellow oil (623 mg, 85%). Column chromatography (CH₂Cl₂/MeOH, 99:1) gave the title compound as yellow oil, MS (electrospray) 393 (M+1).

Example 9

Preparation of

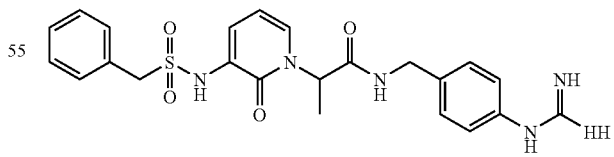

A solution of the product of Example 8 (100 mg, 0.255 mmol) in a mixture of CH₂Cl₂/TFA (1:1, 2 mL) was stirred at room temperature for 90 minutes. The solvent was removed in vacuo to give a transparent oil. This oil was added to a stirring solution of N-[(4-aminomethyl)phenyl]-N'-tert-butoxycarbonyl guanidine (60 mg, 0.223 mmol), HATU (170 mg, 0.446 mmol), and DIEA (123 μL, 0.669 mmol) in acetonitrile (5.0 mL) and the mixture was stirred at room temperature overnight. The solvent was removed in vacuo to give an oil. This oil was treated with CH₂Cl₂/TFA (1:1, 2 mL) and then was stirred at room temperature for 90 minutes. The solvent was removed in vacuo to give a transparent oil. HPLC purification (CH₃CN, H₂O, 0.1% TFA) gave a fluffy white solid as the title compound (30 mg), MS (electrospray) 483 (M+1).

Example 10

Preparation of

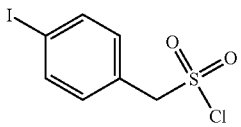

A mixture of thiourea (512 mg, 6.73 mmol) in MeOH (3.5 mL, ~2 M) was heated to near reflux to form a saturated solution. After cooling to room temperature, 4-iodobenzyl bromide (2.0 g, 6.73 mmol) was added and the mixture was allowed to stir overnight. The reaction mixture was diluted with diethyl ether (20 mL) to give a white solid that was removed by filtration. The solid was dissolved in a H₂O/1,4-dioxane mixture (40 mL, 1:1) in an ice bath, treated with chlorine gas for 5 minutes, followed by five minutes treatment with nitrogen. The reaction mixture was diluted with ethyl acetate (40 mL) and washed with H₂O (3×10 mL). The organic layer was dried over Na₂SO₄, filtered and concentrated in vacuo to give an off-white solid (1.8 mg, 85%) which was used in the next step without further purification. ¹H NMR (CDCl₃) δ7.80 (d, 2H), 7.25 (d, 2H), 7.20 (s, 1H), 4.84 (d, 2H).

Example 11

Preparation of

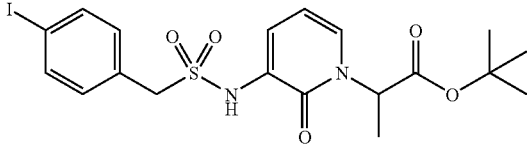

A solution of the product of Example 7 (500 mg, 1.87 mmol), 4-iodobenzylsulfonylchloride (591 mg, 1.87 mmol), and TEA (807 µL, 5.60 mmol) in acetonitrile (10 mL) was stirred at room temperature overnight. The solvent was removed in vacuo and the residual oil was diluted with water (20 mL). The water layer was extracted with CH₂Cl₂ (3×50 mL) and the combined organic layers were dried over Na₂SO₄, solvent was removed to give a yellow oil. Column chromatography (CH₂Cl₂/MeOH, 99:1) gave the title compound as yellow oil that solidified upon standing, MS (electrospray) 519 (M+1).

Example 12

Preparation of

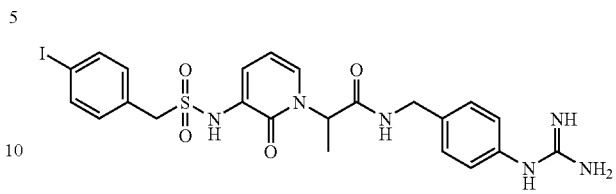

A solution of the product of Example 11 (50 mg, 0.0965 mmol) in a mixture of CH₂Cl₂/TFA (1:1, 2 mL) was stirred at room temperature for 90 minutes. The solvent was removed in vacuo to give a transparent oil. This oil was added to a stirring solution of N-[(4-aminometyl)phenyl]-N'-tert-butoxycarbonyl guanidine (17 mg, 0.0649 mmol), HATU (50 mg, 0.129 mmol), and DIEA (36 µL, 0.195 mmol) in acetonitrile (5.0 mL) and the mixture was stirred overnight at room temperature. The solvent was removed in vacuo to an oil. This oil was treated with CH₂Cl₂/TFA (1:1, 2 mL) for 90 minutes. The solvent was removed in vacuo to give a transparent oil. HPLC purification (CH₃CN, H₂O, 0.1% TFA) gave a fluffy white solid as the title compound (30 mg), MS (electrospray) 609 (M+1).

Example 13

Preparation of

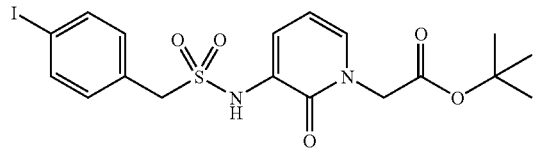

A solution of 2-(3-amino-2-oxo-2H-pyridin-1-yl)-acetic acid tert-butyl ester (300 mg, 1.34 mmol), 4-iodobenzylsulfonylchloride (381 mg, 1.20 mmol), and TEA (346 µL, 2.40 mmol) in acetonitrile (5 mL) was stirred at room temperature overnight. The solvent was removed in vacuo and the residual oil was diluted with water (20 mL). The water layer was extracted with CH₂Cl₂ (3×50 mL) and the combined organic layers were dried over Na₂SO₄; solvent was removed to give a yellow oil. Column chromatography (CH₂Cl₂/MeOH, 99:1) gave the title compound as yellow oil that solidified upon standing (300 mg, 44%), MS (electrospray) 505 (M+1).

Example 14

Preparation of

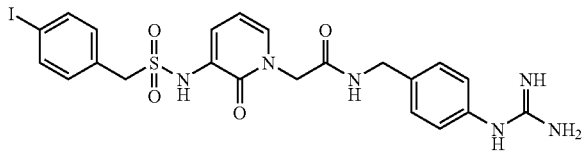

A solution of the product of Example 13 (100 mg, 0.198 mmol) in a mixture of CH₂Cl₂/TFA (1:1, 2 mL) was stirred at room temperature for 90 minutes. The solvent was removed in vacuo to give a transparent oil. This oil was added to a stirring solution of N-[(4-aminomethyl)phenyl]-N'-tert-butoxycarbonyl guanidine (42 mg, 0.156 mmol), HATU (119 mg, 0.313 mmol), and DIEA (87 µL, 0.469 mmol) in acetonitrile (5.0 mL) and the mixture was stirred room temperature overnight. The solvent was removed in vacuo to an oil. This oil was treated with CH$_2$Cl$_2$/TFA (1:1, 2 mL for 90 minutes. The solvent was removed in vacuo to give a transparent oil. HPLC purification (CH$_3$CN, H$_2$O, 0.1% TFA) gave the title compound as a fluffy white solid (50 mg), MS (electrospray) 595 (M+1).

Example 15

Preparation of

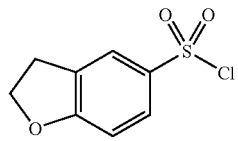

2,3-Dihydrobenzo[b]furan (Aldrich, 5.6 mL, 50 mmol) was added to a suspension of sulfur trioxide-dimethylformamide complex (Aldrich, 9.2 g, 60 mmol) in 1,2-dichloroethane (Aldrich, 20 mL). After being heated at 80° C. for 1 hour, the reaction mixture was cooled to room temperature, and thionyl chloride (Aldrich, 4.5 mL, 57 mmol) was introduced. The reaction mixture was then heated at 70° C. for 3 hours. After cooling to room temperature, the reaction mixture was poured into ice water (100 mL) and extracted with ether (3×30 mL). Combined organic layers were washed with brine, then dried (MgSO$_4$). Removal of solvent under vacuum yielded a light yellow solid (10.2 g, 94%). TLC R$_f$ 0.45 (9:1 of hexane-ethyl acetate); MS (electrospray) 219 (M+1); $^1$H NMR (CDCl$_3$) δ3.35 (t, 2H, J=7.2 Hz), 4.78 (t, 2H, J=7.2 Hz), 6.92 (d, 1H, J=3.1 Hz), 7.82 (s, 1H), 7.83 (d, 1H, J=3.1 Hz).

Example 16

Preparation of

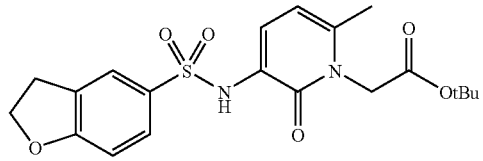

A solution of the product of Example 15 (1.8 g, 8.3 mmol), 3-amino-6-methyl-1-tert-butylmethylenecarboxy-2-pyridinone (synthesized based on a literature procedure: Sanderson, P. E. J., et al., *J. Med. Chem.* 1998, 41, 4466-4474; 1.5 g, 6.4 mmol ), and triethylamine (Aldrich, 4.5 mL, 32 mmol) in acetonitrile (20 mL) was stirred at room temperature for 16 hours. The solvent was removed under vacuum and the residue was purified by flash chromatography (40:60 of hexane-ethyl acetate) to give the title compound as a white solid (1.7 g, 64%). MS (electrospray) 421 (M+1).

Example 17

Preparation of

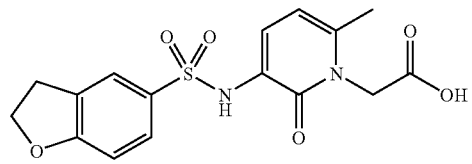

A solution of hydrogen chloride in dioxane (Aldrich, 4.0M, 10 mL) was added to a solution of the product of Example 16 (750 mg, 1.8 mmol) in dioxane (10 mL), and the mixture was stirred at room temperature for 4 hours. The solvent was removed under vacuum to give the title compound (590 mg, 100%), which was used in the next step without further purification. MS(electrospray) 365 (M+1).

Example 18

Preparation of

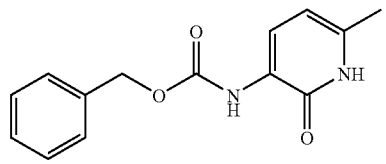

To a solution of 75.0 g (163.2 mmol) 2-hydroxy,6-methyl nicotinic acid in 200 mL acetone, was added 50 mL (359.0 mmol) triethylamine under a nitrogen atmosphere. The reaction mixture was cooled to −5° C. and 55.7 g (326.4 mmol) benzyl chloroformate in 50 mL of acetone was added over 30 minutes. The reaction mixture was stirred for 30 minutes at 0° C. and then cooled to −5° C. A solution of 21.2 g (326.4 mmol) sodium azide in 75 mL water was added to the reaction mixture over 10 minutes. The resulting mixture was stirred for 1 hour at 3° C. The reaction mixture was then poured into 700 mL ice water and let to warm to room temperature. The aqueous solution was extracted 3 times with 250 mL toluene. The organic phases were combined and dried over anhydrous sodium sulfate. The sodium sulfate was filtered away and the organic layer was concentrated to remove the acetone. The resulting solution of toluene was heated to 65° C. for 16 hours. The reaction mixture was cooled to room temperature and was then concentrated under vacuum. The remaining residue was dissolved in 100 mL acetonitrile. Once a homogeneous solution formed, 100 mL (100 mmol) of 1N NaOH was added. The resulting solution was stirred for 1 hour at room temperature. To the reaction mixture was added 100 mL isopropanol, at which time the product precipitated out of solution. The solid product was isolated via filtration. Further purification was completed by recrystallization from isopropyl alcohol or by flash chromatography (silica, 0 to 4% methanol in dichloromethane). After complete purification, the above-identified product was isolated as an off-white solid, 16.0 g (38%). R$_f$=0.2 (10% ethyl acetate in dichloromethane).

Example 19

Preparation of

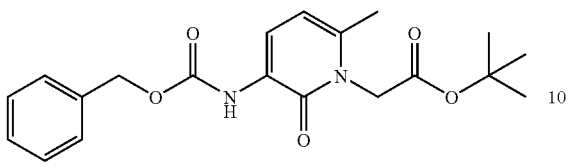

To a solution of the product of Example 18 (10.0 g, 38.7 mmol) in 50 mL anhydrous tetrahydrofuran cooled to 0° C. under a nitrogen atmosphere, was added a 1M solution of lithium bis(trimethylsilyl)amide in tetrahydrofuran (39.1 mL 39.1 mmol) over 40 minutes. The ice bath was removed and the reaction mixture was stirred for 1.5 hours at room temperature. The reaction mixture was then cooled to 10° C. and 5.72 mL (38.7 mmol) t-butyl bromoacetate was added in two portions. The reaction mixture was stirred for 16 hours at room temperature. The reaction was quenched with 1.0 mL of water. The solution was concentrated under vacuum. The residue was dissolved in 200 mL ethyl acetate and washed sequentially with 50 mL 1N hydrochloric acid, saturated aqueous sodium bicarbonate, water, and brine. The organic layer was dried over anhydrous sodium sulfate. The sodium sulfate was filtered away and the organic solution was concentrated under vacuum. The resulting oil was triturated twice with 200 mL of hexane and once with 200 mL of 1:1 hexane/diethyl ether. The solvent was removed under vacuum to afford 11.7 g (81% yield) of the above-identified product. $^1$H NMR (CDCl$_3$) δ1.48 (s, 9H), 2.24 (s, 3H), 4.75 (s, 2H), 5.20 (s, 2H), 6.10 (d, 1 H), 7.35 (m, 5H), 7.35 (d, 1H).

Example 20

Preparation of

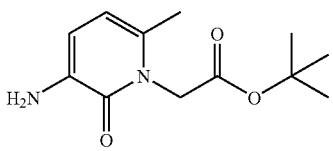

To a solution of the product of Example 19 (25.0 g, 67.1 mmol) in 280 mL methanol/water (4:1, V/V) under a nitrogen atmosphere, was added 2.5 g 20% palladium(II) hydroxide on carbon. The reaction mixture was hydrogenated at 40 psi for 4 hours. Thin layer chromatography (5% methanol in dichloromethane) revealed no more starting material was present. The catalyst was filtered off and washed with methanol. The organic solution was concentrated under vacuum to afford 15.77 g (98%) of the above-identified product as a light yellow solid. $R_f$=0.4 (5% methanol in dichloromethane).

Example 21

Preparation of

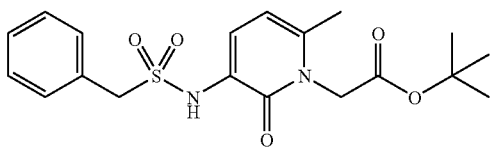

To a solution of the product of Example 20 (25.0 g, 67.1 mmol) in 200 mL of acetonitrile, was added 20.69 g (131.08 mmol) of benzyl sulfonyl chloride. Once the solution became homogeneous, 13.1 mL (99.4 mmol) of 2,4,6-collidine was added. The reaction mixture stirred 72 hours at room temperature. Thin layer chromatography using a solution of 5% methanol in dichloromethane revealed no starting material was present. The solvent was removed under vacuum. The resulting residue was dissolved in 400 mL dichloromethane and washed subsequently with 0.5 M hydrochloric acid and brine. The organic layer was dried over anhydrous magnesium sulfate. The magnesium sulfate was filtered away and the solution was concentrated under vacuum. The crude product was purified by flash chromatography (silica, 3 to 5% methanol in dichloromethane). The above-identified product was isolated as a light brown solid, 13.6 g (77%). $R_f$=0.66 (5% methanol in dichloromethane).

Example 22

Preparation of

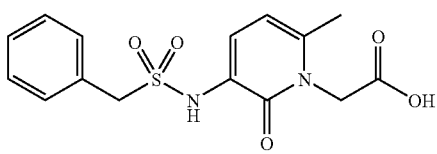

The product of Example 21 (13.6 g, 34.65 mmol) was dissolved in 50 mL 50% trifluoroacetic acid in dichloromethane and stirred at room temperature for 4 hours. The solvent was evaporated under vacuum. A solution of dichloromethane and toluene was added as an azeotrope. The solution was concentrated under vacuum to afford 13.6 g of the above-identified product as a light brown solid.

Example 23

Preparation of

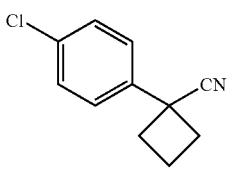

A solution of 4-chlorophenylacetonitrile (4.0 g, 26.4 mmol) and 1-bromo-3-chloropropane (4.6 g, 29 mmol) in anhydrous dimethylsulfoxide (6.0 mL) was added to a suspension of sodium hydride 60% oil dispersion (2.3 g, 58.1 mmol) in anhydrous dimethylsulfoxide (20 mL) at ambient temperature over 10 minutes. Foaming was observed. After 15 minutes, an additional 5 mL of anhydrous dimethylsulfoxide was added to aid in stirring. After 48 hours, the reaction was quenched by the addition of water until no further gas was evolved. Then the product was extracted into ether (2×100 mL), was washed with 1N HCl (50 mL), and brine (50 mL), and was dried over magnesium sulfate. Purification by silica gel chromatography eluting with a hexanes:ethyl acetate gradient (19:1 to 9:1) gave the title compound (1.59 g) as a clear liquid. Rf (Hexane: EtOAc 1:1)=0.61.

Example 24

Preparation of

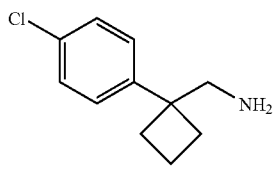

To a solution of the product of Example 23 (2.0 g, 10.4 mmol) in tetrahydrofuran at 0° C. was added lithium aluminum hydride (1M in THF, 11.0 mL). After 2 hours, 0.46 mL water was added, followed by addition of 0.46 mL 3N sodium hydroxide and then 1.38 mL water. The reaction mixture was filtered through celite. The solids were washed with tetrahydrofuran, and the filtrate was concentrated to give the titled amine as a clear oil (1.8 g). Rf (Hexane: EtOAc 1:1)=0.02.

Example 25

Preparation of

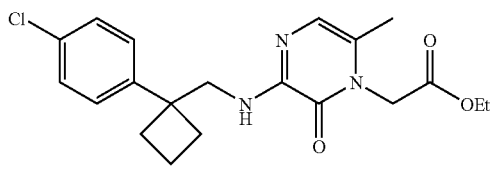

The product of Example 24 (1.8 g, 9.2 mmol) and ethyl 2-bromo-1-pyrazinone acetate (2.1 g, 7.7 mmol) were suspended in dioxane (25 mL). Triethylamine (1.6 mL, 11.6 mmol) was added and the reaction mixture was heated in an oil bath at 95° C. for 2 days. After cooling to ambient temperature, the reaction mixture was diluted with water (20 mL) and concentrated to remove the dioxane. The residue was extracted with dichloromethane (2×100 mL), washed with ammonium chloride solution (75 mL) and brine (75 mL), and dried over magnesium sulfate. The title compound was purified by silica gel chromatography eluting with 2% methanol:dichloromethane to yield 2.95 g of product as a brown oil. Rf (5% MeOH: DCM)=0.39.

Example 26

Preparation of

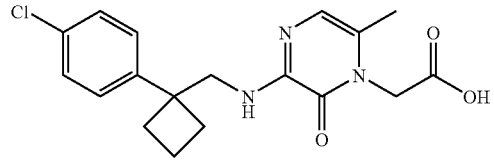

The product of Example 25 (2.9 g, 7.4 mmol) was dissolved in ethanol. 1N lithium hydroxide (22 mL, 22 mmol) was added. The reaction mixture was stirred at ambient temperature for 40 hours. The reaction mixture was concentrated to remove ethanol. The remaining aqueous solution was extracted with diethyl ether, then acidified to pH=3, and extracted into ethyl acetate (75 mL) and dichloromethane (75 mL), then washed with brine (50 mL) and dried over magnesium sulfate. Concentration gave an orange foam which was triturated with a mixture of hexanes and ethyl acetate 9:1 to give the title compound 1.63 g as a pale orange solid. Rf (10% MeOH:DCM)=0.13.

Example 27

Preparation of

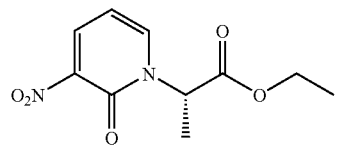

NaH (60% in oil, 629 mg, 16 mmol) was added in portions (over 5 minutes) to a stirring solution of 2-hydroxy-3-nitropyridine (2.0 g, 14 mmol) in DMF (100 mL). To this reaction mixture was added ethyl (R)-(+)-2-[(trifluoromethylsulfonyl)oxy]propionate (3.2 mL, 17 mmol) and the mixture was stirred overnight. The solvent was removed in vacuo. Column chromatography (CH$_2$Cl$_2$/MeOH, 99:1) gave the title compound as a yellow solid (1.5 g, 87%), [α]$_D$=−81 (c=1.0, CH$_2$Cl$_2$), MS (electrospray) 241 (M+1).

Example 28

Preparation of

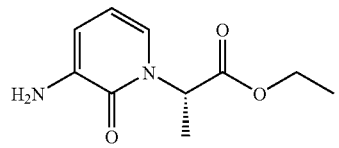

A solution of the product of Example 27 (1.5 g, 6.3 mmol) and PdOH (15% on carbon, 200 mg) in MeOH (10 mL) was shaken under H$_2$ (30 psi) for 3 hours. The catalyst was removed by filtration and the solvent was removed in vacuo to give an oil corresponding to the title compound, MS (electrospray) 211 (M+1).

Example 29

Preparation of

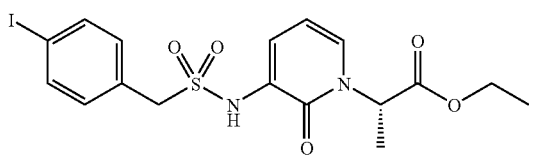

A solution of the product of Example 28 (398 mg, 1.90 mmol), 4-iodo-benzylsulfonylchloride (500 mg, 1.58 mmol), and TEA (912 μL, 6.32 mmol) in acetonitrile (5 mL) was stirred at room temperature overnight. The solvent was removed in vacuo and the residual oil was diluted with water (20 mL). The water layer was extracted with $CH_2Cl_2$ (3×50 mL) and the combined organic layers were dried over $Na_2SO_4$, and removed to give an yellow oil (180 mg, 236). Column chromatography (EtOAc/Hexanes, 1:3) gave the title compound as a transparent oil, $[\alpha]_D=-29$ (c=1.0, $CH_2Cl_2$), MS (electrospray) 491 (M+1)

Example 30

Preparation of

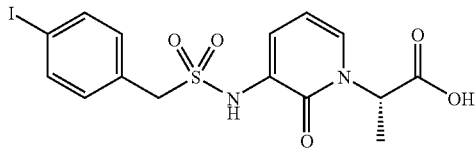

LiOH (62 mg, 42 mmol) was added to a stirring solution of the product of Example 29 in dioxane/$H_2O$ (4:1, 4.0 mL) and the mixture was stirred at room temperature overnight. The solution was acidified using Dowex 50 WX8-400. The solid was removed by filtration and the solvent was removed in vacuo to give an oil corresponding to the title compound.

Example 31

Preparation of

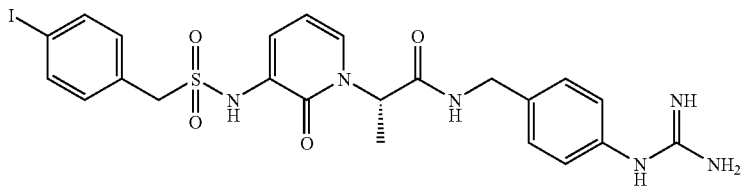

A solution of the product of Example 30 (170 mg, 0.367 mmol), N-[(4-aminometyl)phenyl]-N'-tert-butoxycarbonyl guanidine (97 mg, 0.367 mmol), HATU (279 mg, 0.734 mmol), HOAT (99 mg, 0.734 mmol) and DIEA (270 μL, 1.47 mmol) in acetonitrile (2.0 mL) was stirred at room temperature overnight. The solvent was removed in vacuo to give an oil. This oil was treated with $CH_2Cl_2$/TFA (1:1, 5 mL) and stirred at room temperature for 90 minutes. The solvent was removed in vacuo to give a transparent oil. HPLC purification ($CH_3CN$, $H_2O$, 0.1% THF) gave a fluffy white solid as the title compound (55 mg), $[\alpha]_D=-7.5$ (c=1.0, MeOH), MS (electrospray) 609 (M+1).

Example 32

Preparation of

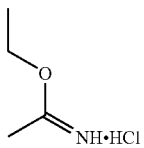

Dry HCl(g) was gently bubbled through a solution of acetonitrile (7.6 mL, 235 mmol) in dry ethanol (18 mL) at 0° C. over a period of four hours. The resulting clear solution was let to stand at room temperature for approximately 18 hours. The solution was concentrated under reduced pressure and dried in vacuo to yield a white solid which was used in the next step without further purification (25.3 g, 88.2%).

Example 33

Preparation of D-Cysteine Methylester Hydrochloride Salt

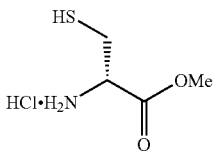

D-Cysteine (3 g, 17 mmol) was dissolved in a saturated solution of dry HCl(g) in anhydrous methanol and was refluxed for 18 hours. The reaction mixture was concentrated under reduced pressure and dried in vacuo to a viscous oil (quantitative yield). $^1H$ NMR (δ, $CDCl_3$, ppm): 4.4 (t, 1H), 3.7 (s, 3H), 3.1 (dd, 1H), 3.0 (dd, 1H).

Example 34

Preparation of

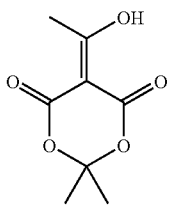

To a solution of Meldrum's acid (2,2-dimethyl-[1,3]dioxane-4,6-dione) (3.3 g, 23 mmol) and dimethylaminopyridine (5.3 g, 43 mmol) in dichloromethane (45 mL) at −10° C., was added a solution of acetylchloride (1.63 g, 20.7 mmol) in dichloromethane (18 mL) over 30 minutes. The reaction mixture was warmed to room temperature and stirred for four hours. It was then diluted with dichloromethane (50 mL) and washed successively with 50 mL portions of potassium bisulfate (×2), HCl(1N), water (×2) and brine. The individual aqueous fractions were back-extracted with dichloromethane and the combined organic layers were dried over sodium sulfate, filtered and concentrated to yield a solid (60%). $^1$H NMR (δ, CDCl$_3$, ppm); 2.68 (s, 3H), 1.79 (s, 6H).

Example 35

Preparation of

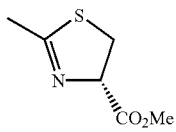

Triethylamine (0.9 mL, 6.41 mmol) was slowly added to a suspension of the product of Example 33 (1.1 g, 6.4 mmol) in anhydrous dichloromethane (7.5 mL) at 0° C. After stirring for 20 minutes, a suspension of the product of Example 32 (600 mg, 6.41 mmol) in dichloromethane (2.5 mL) was added and the reaction mixture was stirred at room temperature for 18 hours. The white milky solution was then diluted with dichloromethane (50 mL) and washed successively with 50 mL portions of water, sodium bicarbonate (saturated) and brine. The aqueous washings were back extracted with dichloromethane. The combined organic layers were dried (Na$_2$SO$_4$) and filtered. The filtrate was concentrated to a colorless oil (0.6 g, 58%). $^1$H NMR (δ, CDCl$_3$, ppm): 5.1 (m, 1H), 3.7 (s, 3H), 3.5-3.7 (m, 2H), 2.1 (s, 3H).

Example 36

Preparation of

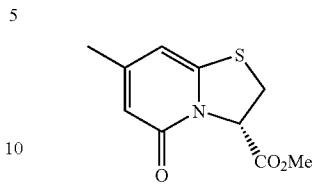

HCl(g) was first bubbled gently through dry sulfuric acid and then into a flask containing a solution of the product of Example 35 (250 mg, 1.56 mmol) and the product of Example 34 (400 mg, 1.56 mmol) in 1,2-dichloroethane (14 mL) at 0° C. for 15 minutes. The ice bath was then removed and the reaction mixture was refluxed at 64° C. overnight. To the resulting yellow solution was added 0.5 equivalents more of the product of Example 34 and the reaction was allowed to continue for two more hours. After cooling to room temperature, the reaction mixture was diluted with dichloromethane and washed successively with 30 mL portions of water, sodium bicarbonate (saturated) and brine. The combined organic extracts were dried over sodium sulfate, filtered and concentrated to a yellow oil (329 mg crude). The crude product was purified by flash column chromatography in ethylacetate: hexane (7:3) (210 mg, 60%). Analytical HPLC using a 4.6×250 mm reverse phase column, containing a C-18 resin comprised of 5 micron size gel particles with a 300 angstrom pore size ran at 5-50% acetonitrile (containing 0.1% trifluoroacetic acid) showed predominantly one peak with the retention time of 12.5 min. Low resolution mass spectroscopy confirmed the desired mass (MH$^+$ 226.1). $^1$H NMR (δ, CDCl$_3$, ppm): 6.1 (d, 1H), 6.0 (d, 1H), 5.55 (dd, 1H), 3.8 (s, 3H), 3.7-3.75 (m, 4H), 3.6 (dd, 1H), 2.1 (s, 3H).

Example 37

Preparation of

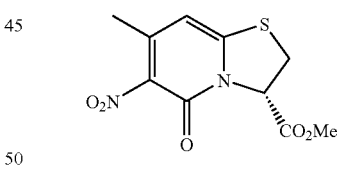

To a stirred mixture of nitric acid (2.1 mL, 95%) and acetic anhydride (0.5 mL) cooled to −12° C., was added dropwise a solution of the product of Example 36 (210 mg, 0.93 mmol) in acetic anhydride (0.5 mL). After two hours, HPLC showed complete transformation; the solution was poured into ice/water and filtered. The yellow filtrate was extracted successively with 15 mL portions of ethylacetate (×4). The combined organic layers were washed with saturated sodium bicarbonate (×2) and brine. The organic layer was dried over sodium sulfate, filtered and concentrated under reduced pressure to a yellowish foam (250 mg crude). The crude material was then purified by flash column chromatography using ethyl acetate: hexane (7:3) as eluant to yield a yellowish foam (66 mg, 65%). Analytical HPLC of the crude using a 4.6×250 mm reverse phase column, containing a C-18 resin comprised of 5 micron size gel

Example 38

Preparation of

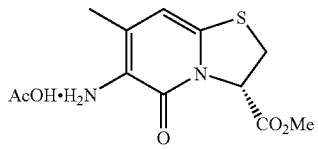

A solution of the product of Example 37 (64 mg, 0.24 mmol) in acetic acid (0.7 mL) was added to a stirred solution of iron powder (160 mg) in acetic acid (0.7 mL). After 1 hour, completion of the reaction was confirmed by HPLC. The reaction mixture was diluted with water and neutralized with solid sodium bicarbonate (pH~7). The aqueous mixture was filtered and then extracted with ethylacetate (4×10 mL). The resulting organic extracts were pooled and washed with brine (2×10 mL). The organic layer was dried over sodium sulfate, filtered and concentrated to a black oil which was used in the next step without further purification. Analytical HPLC of the crude product using a 4.6×250 mm reverse phase column, containing a C-18 resin comprised of 5 micron size gel particles with a 300 angstrom pore size ran at 5-50% acetonitrile (containing 0.1% trifluoroacetic acid) showed predominantly one peak with the retention time of 8 minutes. Low resolution mass spectroscopy confirmed the desired mass (MH$^+$ 241).

Example 39

Preparation of

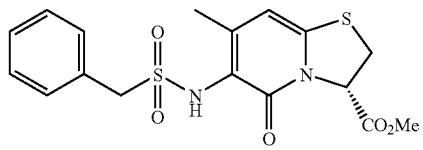

A solution of the product of Example 38 (56 mg, 0.24 mmol), benzylsulfonylchloride (50 mg, 0.26 mmol), and TEA (0.1 mL) in dichloromethane (2 mL) was stirred at room temperature overnight. The reaction mixture was filtered and the residual solid was discarded. The filtrate was washed successively with ammonium chloride (2×10 mL) and brine (×2). The organic layer was dried over sodium sulfate, filtered and concentrated under reduced pressure to yield 35 mg product. Analytical HPLC of the crude product using a 4.6×250 mm reverse phase column, containing a C-18 resin comprised of 5 micron size gel particles with a 300 angstrom pore size ran at 5-90% acetonitrile (containing 0.1% trifluoroacetic acid) showed predominantly one peak with the retention time of 13 minutes. Low resolution mass spectroscopy confirmed the desired mass (MH$^+$ 395).

Example 40

Preparation of

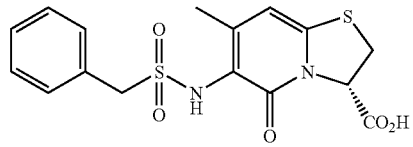

To a solution of the methylester (35 mg, 0.088 mmol) obtained in Example 39 in dioxane (1.3 mL), was added 2N LiOH (0.14 mL). The resulting clear solution was stirred at room temperature for 2 hours and then concentrated under reduced pressure. The remaining residue was redissolved in a mixture of water and methanol (1:1, 4 mL) and passed through a small column packed with Dowex 50WX8-400 ion exchange resin (3 mL, dry). The fractions containing product were identified by HPLC and were pooled and lyophilized to yield 20 mg of a yellow solid. Analytical HPLC using a 4.6×250 mm reverse phase column, containing a C-18 resin comprised of 5 micron size gel particles with a 300 angstrom pore size ran at 5-90% acetonitrile (containing 0.1% trifluoroacetic acid) showed one peak with the retention time of 11.5 minutes. Low resolution mass spectroscopy confirmed the desired mass (MH+ 381).

Example 41

Preparation of

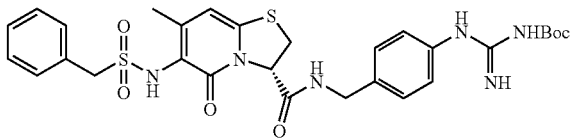

The product obtained in Example 40 (16 mg, 0.042 mmol), N-[(4-aminometyl)phenyl]-N'-tert-butoxycarbonyl guanidine (the product of Example 3) (12 mg, 0.042 mmol), HATU (24 mg, 0.063 mmol), HOAt (10 mg, 0.063 mmol) and DIEA (30 μL, mmol) in acetonitrile (2 mL) were stirred at room temperature for 2.5 hours. The solvent was removed in vacuo and the remaining residue was dissolved in ethylacetate and was washed with saturated ammonium chloride (2×10 mL), and brine (1×10 mL). The organic layer was dried over sodium sulfate, filtered and concentrated to a yellow semisolid material which was used in the next step (Example 42) without further purification. Low resolution mass spectroscopy confirmed the desired mass (MH+ 627).

Example 42

Preparation of

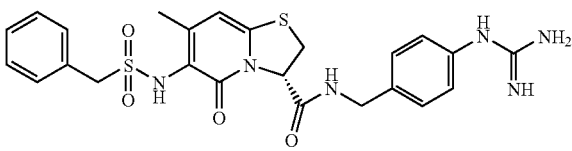

To a chilled solution of the product obtained in Example 41 (20 mg, 0.031 mmol) in dichloromethane (0.8 mL), was added trifluoroacetic acid (1.5 mL). After half an hour at 0° C., the ice bath was removed and the reaction mixture was stirred for two additional hours at room temperature. The reaction mixture was concentrated under reduced pressure and the crude product was purified by reverse phase HPLC (C18). Analytical HPLC using a 4.6×250 mm reverse phase column, containing a C-18 resin comprised of 5 micron size gel particles with a 300 angstrom pore size ran at 5-50% acetonitrile (containing 0.1% trifluoroacetic acid) showed one peak with the retention time of 15 minutes. Low resolution mass spectroscopy confirmed the desired mass (MH+ 527). 1H NMR, $D_2O$, ppm: 7.48-7.44 (m, 5H); 7.41 (d, 2H, 8.8 Hz); 7.07 (d, 2H, 8.8 Hz); 6.48 (s, 1H); 5.64 (dd, 1H, 9.6 Hz, 2.8 Hz); 4.60-4.26 (m, 4H); 4.05 (dd, 1H, 12 Hz, 9.2 Hz); 3.64 (dd, 1H, 12.4 Hz, 2.8 Hz); 2.30 (s, 3H).

Example A

In Vitro Enzyme Assays for Specificity Determination

The ability of compounds of the present invention to act as selective inhibitors of urokinase catalytic activity was assessed by determining the concentration of test compound which inhibited the activity of this enzyme by 50%, ($IC_{50}$), and comparing this value to that determined for all or some of the following related serine proteases: recombinant tissue plasminogen activator (rt-PA), plasmin, activated protein C, chymotrypsin, factor Xa, thrombin and trypsin.

The buffer used for all assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_0$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters (about 4 times Km). The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value. $K_i$ may be calculated from the $IC_{50}$ value.

Urokinase Assay

Urokinase catalytic activity was determined using the chromogenic substrate 150 mM S-2444 (L-Pyroglutamyl-glycyl-L-arginine-p-nitroaniline hydrochloride), obtained from DiaPharma Group, Inc. Urokinase (Abbokinase), manufactured by Abbott Laboratories, was obtained from Priority Pharmaceuticals and diluted to 750 pM in the HBSA assay buffer prior to use. The assay buffer was HBS (10 mM HEPES, 150 mM sodium chloride pH 7.4) with 0.1% BSA. $K_i$ was calculated using the $IC_{50}$ value.

Thrombin (fIIa) Assay

Enzyme activity was determined using the chromogenic substrate, Pefachrome t-PA ($CH_3SO_2$-D-hexahydrotyrosine-glycyl-L-Arginine-p-nitroaniline, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 μL), α-thrombin (50 μl) (the final enzyme concentration is 0.5 nM) and inhibitor (50 μl) (covering a broad concentration range), were combined in appropriate wells and incubated for 30 minutes at room temperature prior to the addition of substrate Pefachrome-t-PA (50 μl) (the final substrate concentration is 250 μM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-nitroaniline ), obtained from DiaPharma Group (Franklin, Ohio). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P., Arch. Biochem. Biophys. 273:375-388 (1989)]. The enzyme was diluted into HBSA prior to assay in which the final concentration was 0.25 nM.

Recombinant Tissue Plasminogen Activator (rt-PA) Assay rt-PA catalytic activity was determined using the substrate, Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 [L-pyroglutamyl-L-prolyl-L-arginine-p-nitroaniline hydrochloride], which was obtained from DiaPharma Group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzyloxy-D-lysine-L-prolyl-L-arginine-p-nitroaniline dihydrochloride), obtained from Pentapharm Ltd.). The substrate was made up in deionized water followed by dilution in HBSA prior to the assay in which the final concentration was 400 micromolar (about 3 times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroanilide), which was obtained from DiaPharma Group. The substrate was made up in deionized water followed by dilution in HBSA prior to the assay in which the final concentration was 100 micromolar (about 9-times Km). Purified (3x-crystallized; CDI) bovine pancreatic α-chymotrypsin was obtained from Worthington Biochemical Corp. The enzyme was reconstituted in deionized water and diluted into HBSA prior to assay in which the final concentration was 0.5 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3x-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table I

Table I lists the determined $K_i$ values for certain of the enzymes listed above for compounds of the present invention that demonstrate a high degree of specificity for the inhibition of urokinase compared to other serine proteases.

TABLE I

| Compound (FIG. 8) | $K_i$ uPA* | $K_i$ hTrypsin* | $K_i$ Plasmin* |
| --- | --- | --- | --- |
| A | C | D | IA |
| B | B | B | IA |
| C | A | C | IA |
| D | B | B | IA |
| E | C | B | IA |
| F | A | B | IA |

*
A = less than 100 nM
B = 100 to 250 nM
C = 250 to 1000 nM
D = 100 to 2500 nM
E = >2500 nM
IA = inactive Example B Evaluation of Test Compound as an Inhibitor of Angiogenesis In Vivo The chicken CAM (chick embryo chorioallantoic membrane) model, a standard angiogenesis assay, is used to evaluate the ability of a test compound to inhibit angiogenesis. This model is an established model for evaluation of activity of a test compound to affect formulation of new blood vessels.

A filter disc saturated with a 0.5 µg/ml solution of basic fibroblast growth factor (bFGF) is placed on the CAM of 10 day old chick embryos to induce angiogenesis. Twenty four hours later, 0 to 1 µg of Test Compound, in a total volume of 100 µl of sterile PBS, is injected intravenously into the embryo. Approximately 48 hours later, the embryos are sacrificed and the filter discs and surrounding CAM tissue are excised for analysis. Angiogenesis is quantitated by counting the number of blood vessel branch points within the confined region of the filter [Brooks, P. C., et al, Methods in Molecular Biology 120:257-269 (1999)]. The angiogenic index is defined as the difference in the number of blood vessel branch points between an experimental group and the untreated, control embryos. Each experimental group will contain 8 to 10 chicken embryos.

Example C

Evaluation of Test Compound to Inhibit the Growth of Human Tumor Cells in a Chick Embryo Model A chicken embryo model is used to evaluate the activity of Test Compound to inhibit the growth of human tumor cells in vivo. A single cell suspension of human fibrosarcoma cells (HT 1080), containing $4 \times 10^5$ cells in a total volume of 40 µl, is applied to 10 day old chick embryos as described by Brooks, et al ("Brooks, P. C., et al, "Integrin $\alpha_v\beta_3$ Antagonists Promote Tumor Regression by Inducing Apoptosis of Angiogenic Blood Vessels", Cell 79:1157-1164 (1994)). Twenty-four hours later 0 to 10 µg of Test Compound are injected intravenously into the embryos. Following this single administration of compound, control and treated embryos are incubated for a total of 7 days and then sacrificed. Tumors are excised, trimmed free of surrounding CAM tissue, and weighed. The wet weights for tumors excised in this experiment are tabulated. Each experimental group will contain 10 to 12 chicken embryos.

We claim:

1. A compound of the formula:

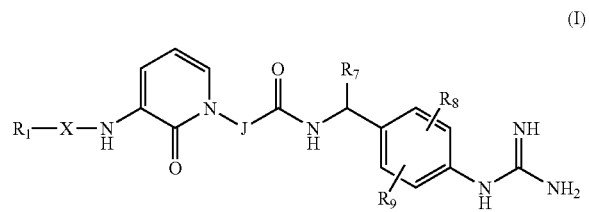

(I)

wherein:
(a) X is $—S(O)_2—$;
(b) $R_1$ is selected from the group consisting of:
   (1) alkyl of 1 to about 12 carbon atoms which is unsubstituted or substituted with 1 to 2 substituents selected from the group consisting of $Y_1$ and $Y_2$,
   (2) alkyl of 1 to about 3 carbon atoms substituted with cycloalkyl of 3 to about 8 carbon atoms which is unsubstituted or mono-, di- or tri-substituted with 1 to 3 substituents selected from the group consisting of $Y_1$, $Y_2$, and/or $Y_3$,
   (3) aryl of about 6 to about 14 carbon atoms which is unsubstituted or mono-, di- or tri-substituted with 1 to 3 substituents selected from the group consisting of $Y_1$, $Y_2$ and $Y_3$,
   (4) aralkyl of about 7 to about 15 carbon atoms which is unsubstituted or substituted on the alkyl chain with hydroxy or halogen and which is unsubstituted or mono-, di- or tri-substituted on the aryl ring with 1 to 3 substituents selected from the group consisting of $Y_1$, $Y_2$ and $Y_3$; wherein each $Y_1$, $Y_2$, and $Y_3$ is independently selected and is
      selected from the group consisting of halogen, cyano, nitro, tetrazolyl, guanidino, amidino, methylguanidino, —CF₃, —CF₂CF₃, —CH(CF₃)₂, —C(OH)(CF₃)₂, —OCF₃, —OCF₂H, —OCF₂CF₃, —OC(O)NH₂, —OC(O)NHZ₁, —OC(O)NZ₁Z₂, —NHC(O)Z₁, —NHC(O)NH₂, —NHC(O)NZ₁, —NHC(O)NZ₁Z₂, —C(O)OH, —C(O)OZ₁, —C(O)NH₂, —C(O)NHZ₁, —C(O)NZ₁Z₂, —P(O)₃H₂, —P(O)₃(Z₁)₂, —S(O)₃H, —S(O)ₘZ₁, —Z₁, —OZ₁, —OH, —NH₂, —NHZ₁, —NZ₁Z₂, —C(=NH)NH₂, —C(=NOH)NH₂, —N-morpholino, and —S(O)ₘ(CF₂)qCF₃, wherein m is 0, 1 or 2, q is an integer from 0 to 5, and Z₁ and Z₂ are independently selected from the group consisting of alkyl of 1 to about 12 carbon atoms, aryl of about 6 to about 14 carbon atoms, aralkyl of about 7 to about 15 carbon atoms, (6) J is —C(R₆ₐ)(R₆ᵦ)— wherein (i) R₆ₐ is in the S configuration and is selected from the group consisting of —CH₃, —CH₂CH₃, —CH₂—S—CH₃, —CH₂OH, —CH₂CN, —CH₂C—CH, —CH₂CH=CH₂, and —CH=CH₂ and R₆ᵦ is hydrogen; or (ii) R₆ᵦ is hydrogen and R₆ₐ is lower alkyl of 1 to about 3 carbon atoms, (d) R₇ is hydrogen or alkyl of 1 to about 4 carbon atoms; and (e) R₈ and R₉ are independently selected from the group consisting of hydrogen, hydroxy, halogen, alkyl of 1 to about 6 carbon atoms, alkyl of 1 to about 4 carbon atoms substituted with alkoxy of 1 to about 4 carbon atoms, alkoxy of 1 to about 6 carbon atoms, and trifluoromethyl; and pharmaceutically acceptable salts thereof.

2. A compound according to claim 1 wherein R₁ is benzyl, substituted benzyl, phenyl or substituted phenyl.

3. A compound according to claim 1 wherein R₁ is aralkyl, substituted aralkyl, aryl, substituted aryl, alkyl, or substituted alkyl.

4. A compound according to claim 1 wherein R₆ₐ is alkyl and R₆ᵦ is hydrogen.

5. A compound according to claim 4 wherein R₆ₐ has the S-configuration.

6. A compound according to claim 4 wherein R₆ₐ is methyl.

7. A compound according to claim 1 wherein R₇ is hydrogen.

8. A compound according to claim 1 wherein R₈ and R₉ are hydrogen.

9. A compound according to claim 1 wherein R₁ is benzyl, substituted benzyl, phenyl, substituted phenyl, alkyl, substituted alkyl, alkyl of 1 to about 3 carbon atoms substituted with cycloalkyl, or alkyl of 1 to about 3 carbon atoms substituted with substituted cycloalkyl.

10. A compound according to claim 1 which is selected from the group consisting of

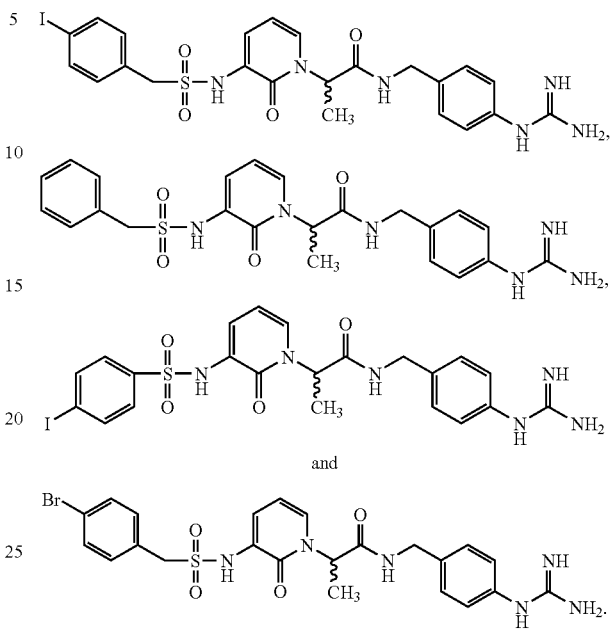

and

11. A pharmaceutical composition comprising a pharmaceutically acceptable carrier and a compound of claim 1.

12. A pharmaceutical composition comprising a pharmaceutically acceptable carrier and a compound of claim 2.

13. A pharmaceutical composition comprising a pharmaceutically acceptable carrier and a compound of claim 3.

14. A pharmaceutical composition comprising a pharmaceutically acceptable carrier and a compound of claim 4.

15. A pharmaceutical composition comprising a pharmaceutically acceptable carrier and a compound of claim 5.

16. A pharmaceutical composition comprising a pharmaceutically acceptable carrier and a compound of claim 6.

17. A pharmaceutical composition comprising a pharmaceutically acceptable carrier and a compound of claim 8.

18. A pharmaceutical composition comprising a pharmaceutically acceptable carrier and a compound of claim 9.

19. A pharmaceutical composition comprising a pharmaceutically acceptable carrier and a compound of claim 10.

* * * * *